United States Patent [19]

Lewicki et al.

[11] Patent Number: 4,757,048

[45] Date of Patent: Jul. 12, 1988

[54] SYNTHETIC ANALOGS OF ATRIAL NATRIURETIC PEPTIDES

[75] Inventors: John A. Lewicki, Sunnyvale; Robert M. Scarborough, Jr., Hayward; Lorin K. Johnson, Pleasanton, all of Calif.

[73] Assignee: Biotechnology Research Associates J.V., Mountain View, Calif.

[21] Appl. No.: 868,312

[22] Filed: May 28, 1986

Related U.S. Application Data

[63] Continuation-in-part of Ser. No. 795,220, Nov. 5, 1985, abandoned.

[51] Int. Cl.$^4$ .................. A61K 37/02; C07K 7/06; C07K 7/08; C07K 7/10
[52] U.S. Cl. .......................................... 514/11; 514/15; 514/14; 514/12; 514/13; 530/324; 530/325; 530/326; 530/327
[58] Field of Search .................. 514/11, 15, 14, 12, 514/13; 530/324, 325, 326, 327

[56] References Cited

U.S. PATENT DOCUMENTS 4,496,544  1/1985  Needleman .................. 530/325
4,508,712  4/1985  Needleman .................. 514/11
4,607,023  8/1986  Thibault et al. ............. 514/11
4,609,725  9/1986  Brady et al. ................. 530/324

FOREIGN PATENT DOCUMENTS 0152333  8/1985  European Pat. Off. .
0172361  2/1986  European Pat. Off. .

OTHER PUBLICATIONS

Chem. Abstr., vol. 102, (1985) 215384.
Science, 223, (1984) 67–69.
Biochem. and Biophys. Res. Commun. 121, (1984) 802–807.

Primary Examiner—Delbert R. Phillips
Attorney, Agent, or Firm—Ciotti & Murashige, Irell & Manella

[57] ABSTRACT

Compounds and compositions comprising synthetic analogs of Atrial Natriuretic Peptides are provided, together with methods for their production and use as natriuretics, diuretics and/or vasodilators, or as intermediates for or modulators of such useful compounds or of native Atrial Natriuretic Peptides.

9 Claims, 7 Drawing Sheets

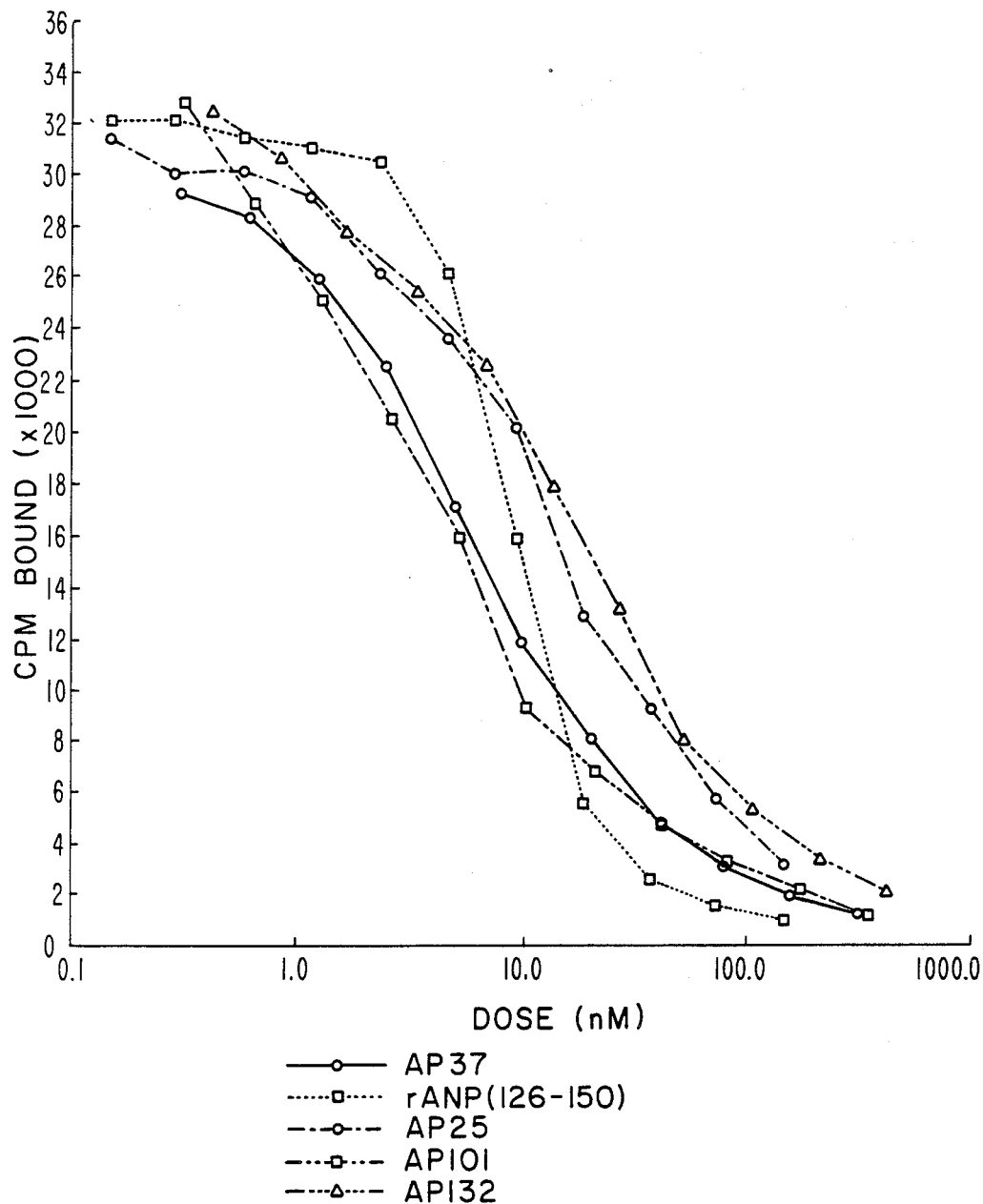

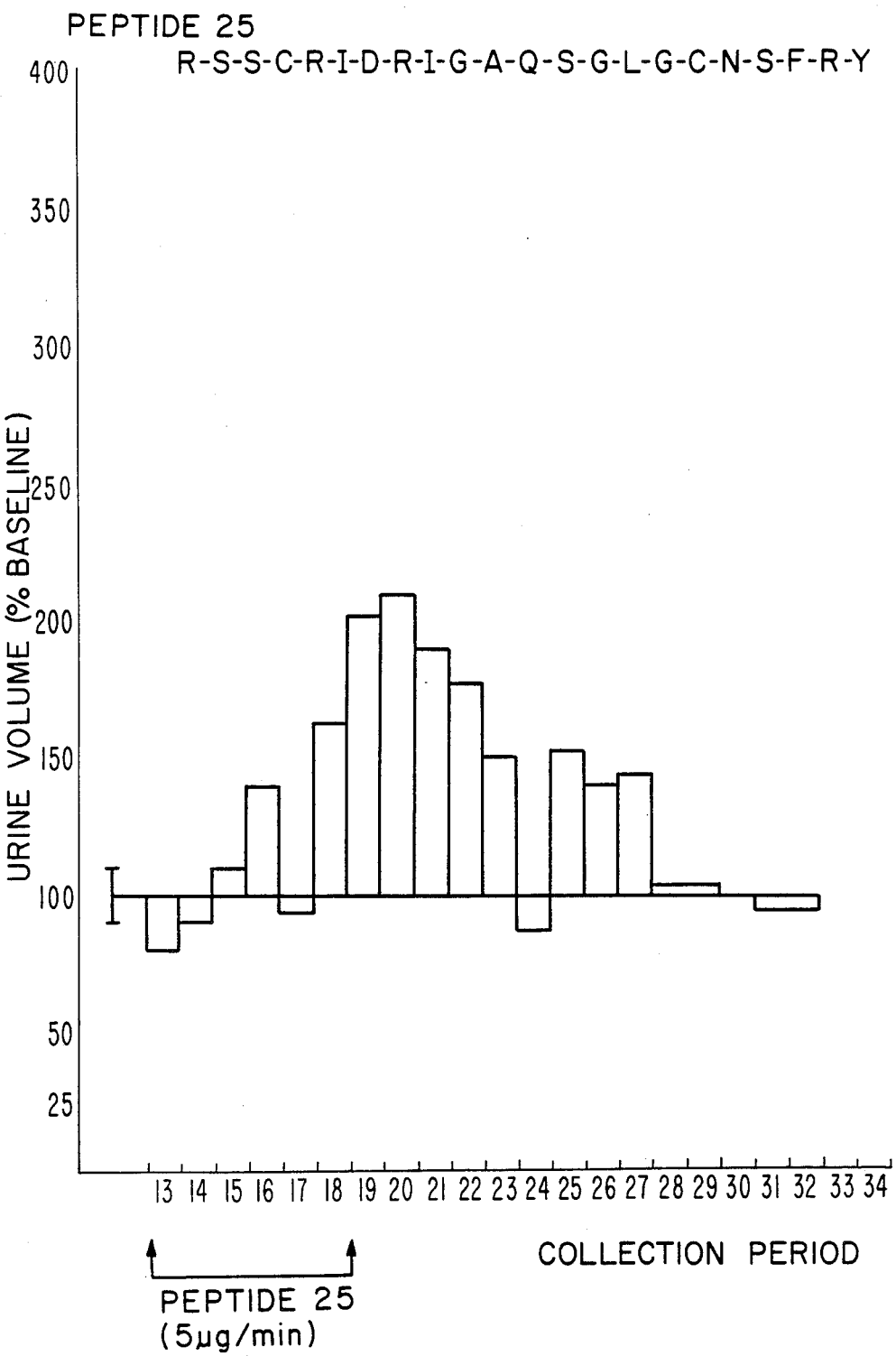

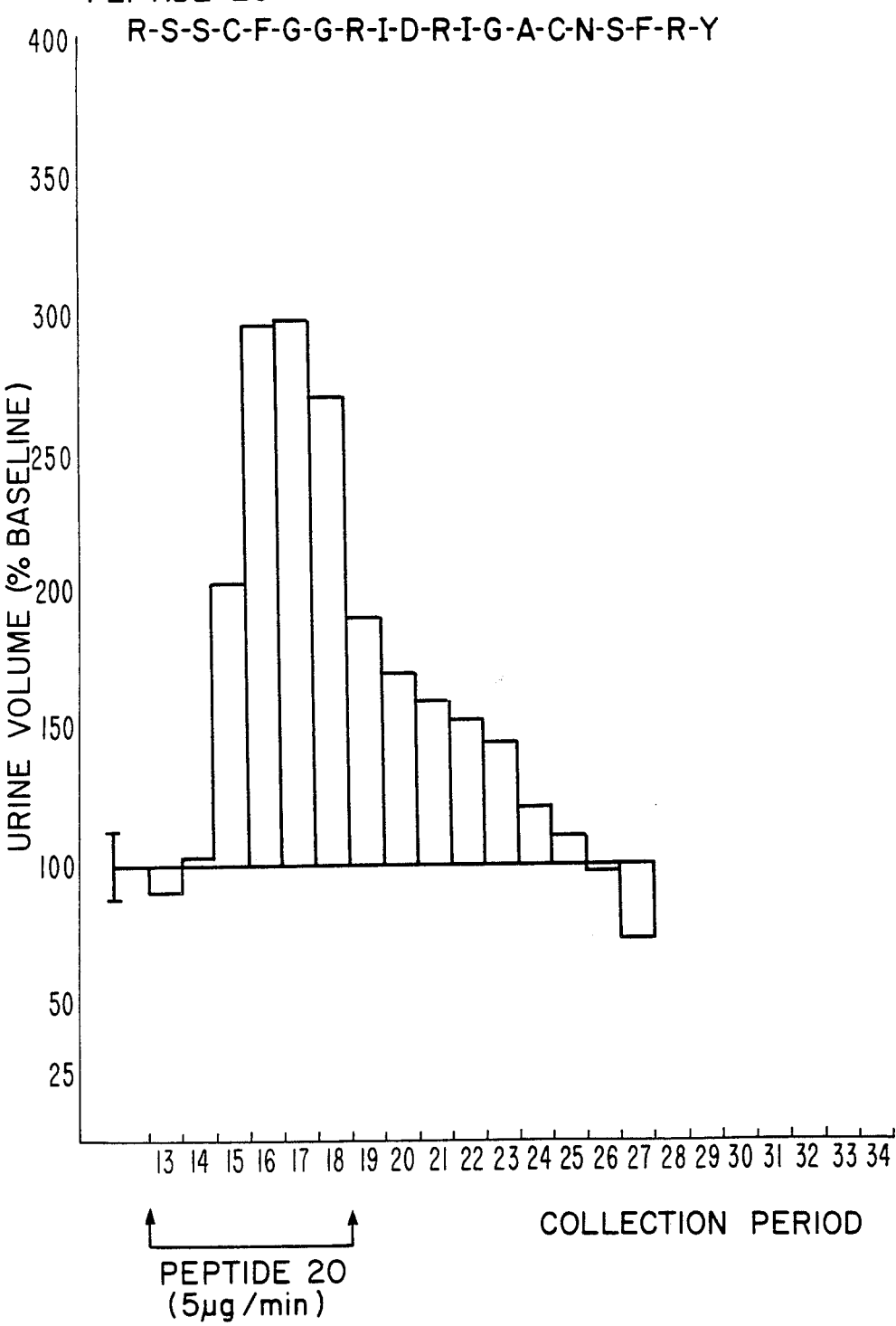

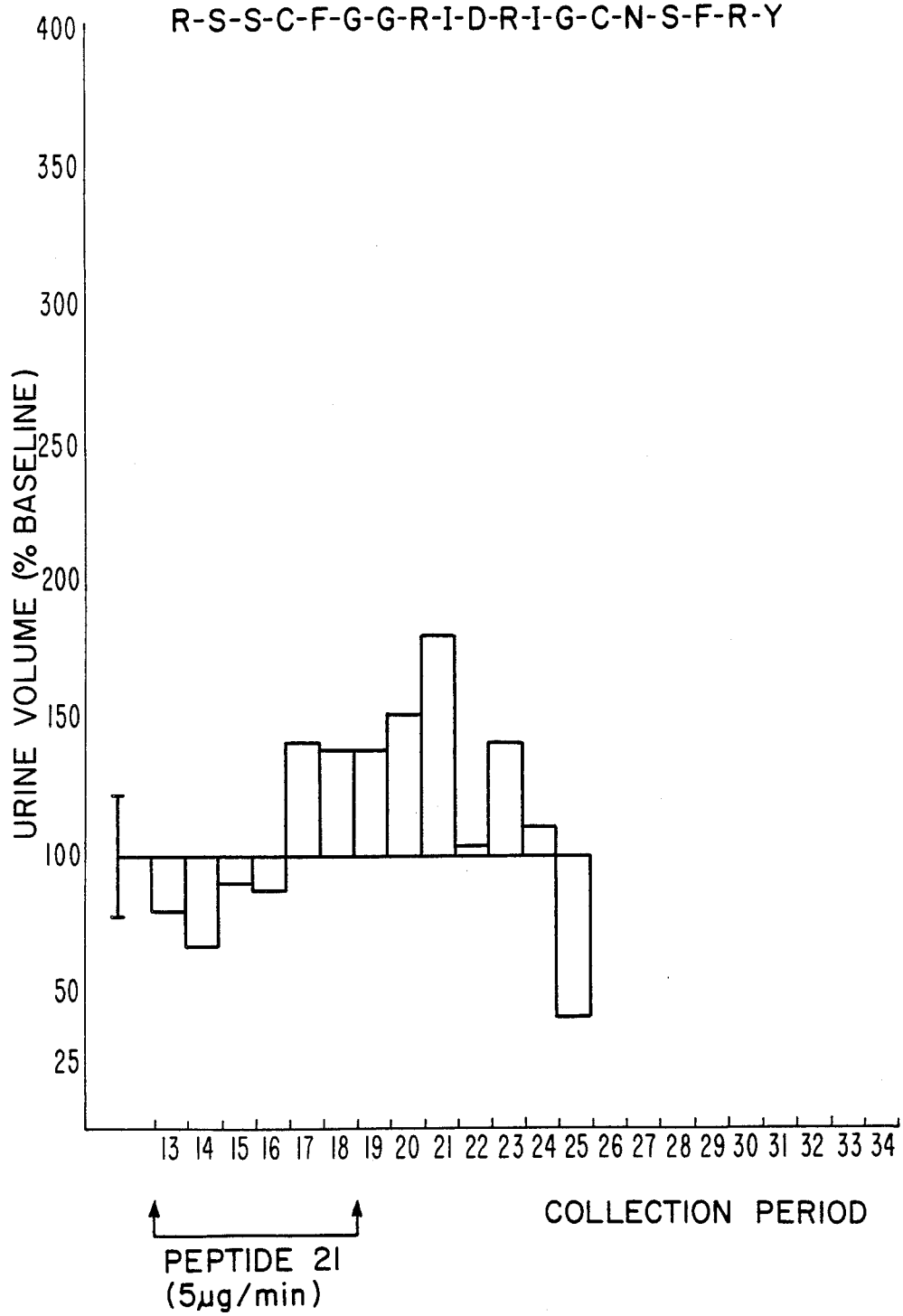

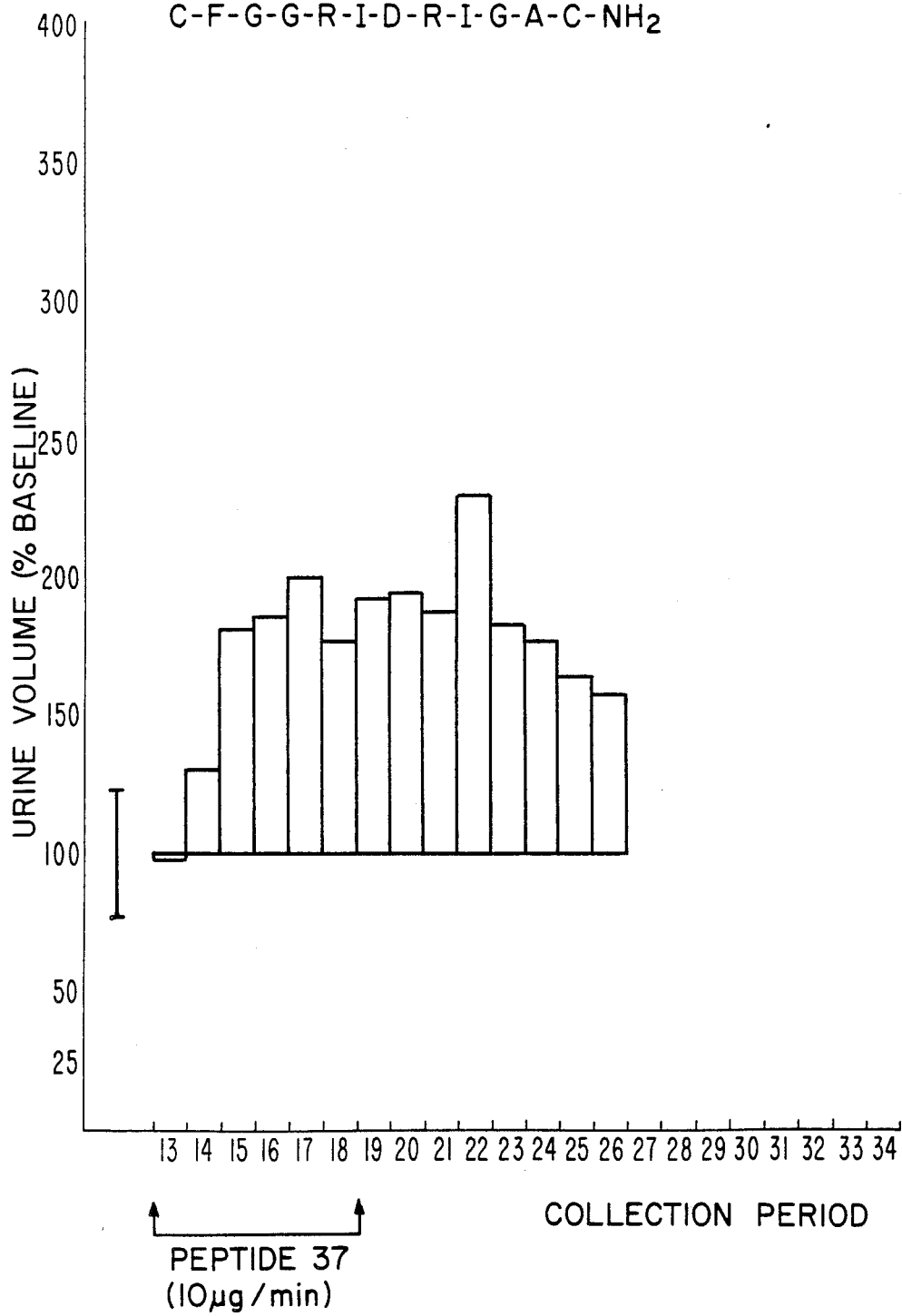

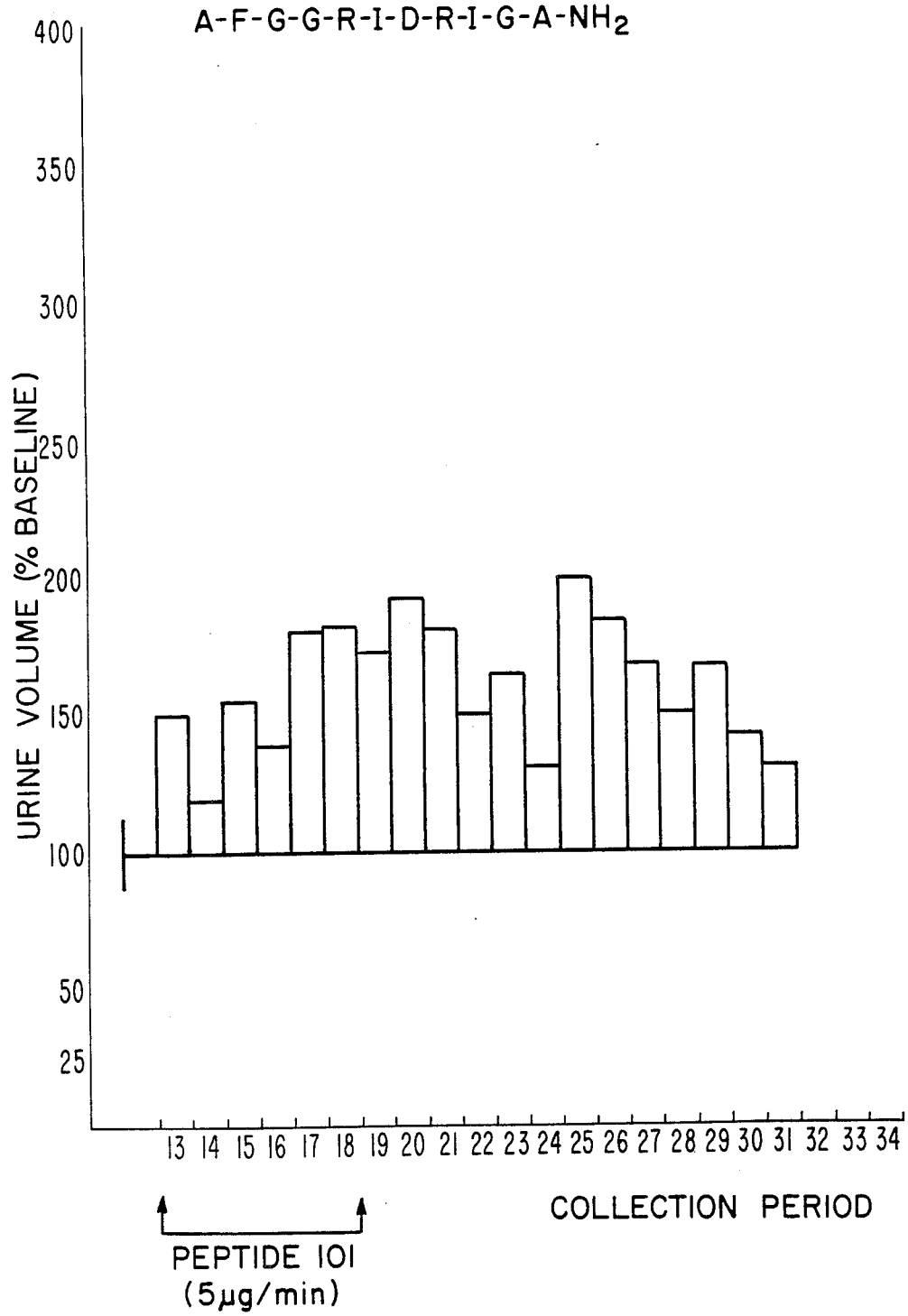

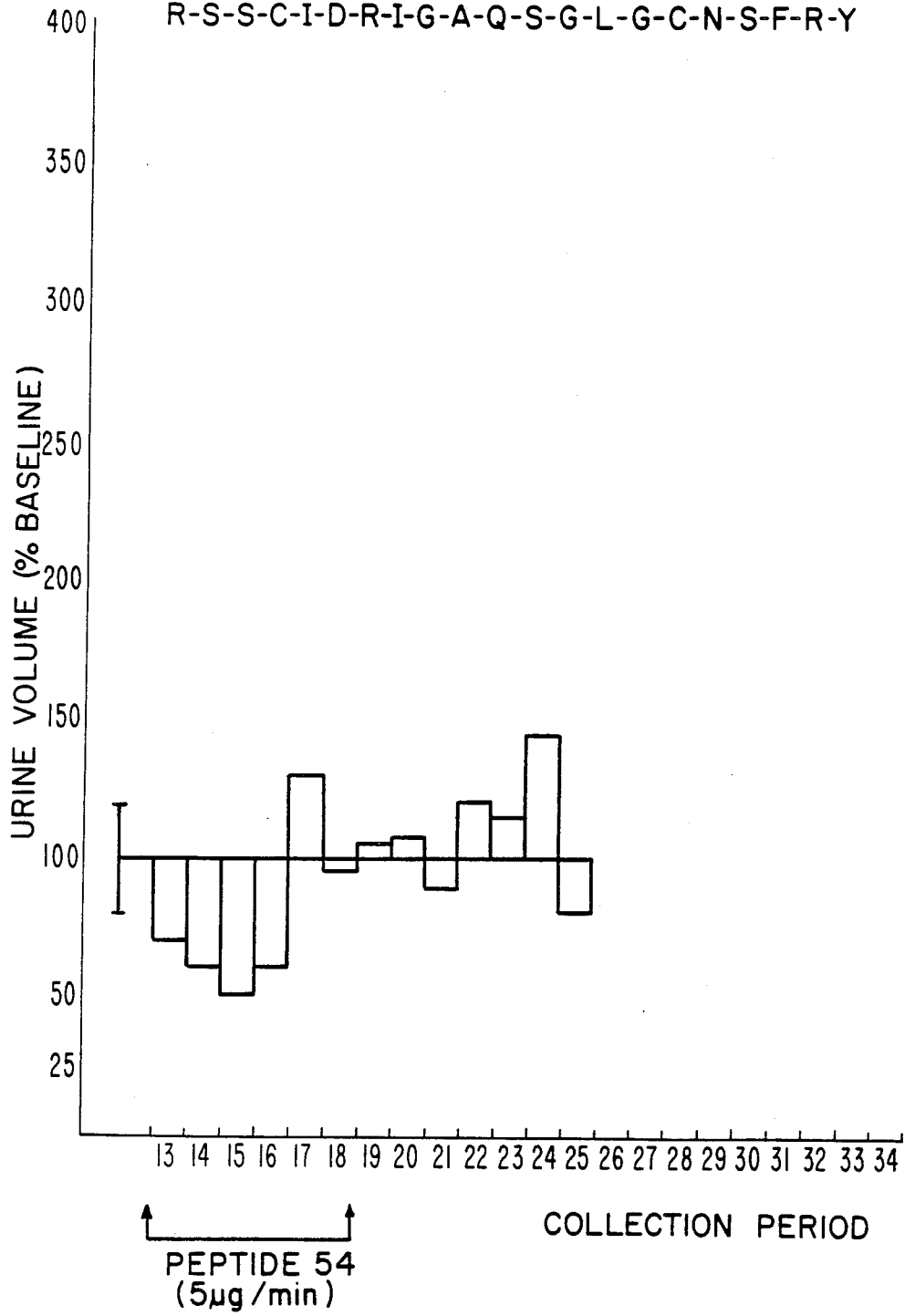

1

SYNTHETIC ANALOGS OF ATRIAL NATRIURETIC PEPTIDES

RELATED APPLICATION DATA

This application is a continuation-in-part of commonly-owned and co-pending application Ser. No. 795,220, filed Nov. 5, 1985, now abandoned.

TECHNICAL FIELD

The present invention relates generally to synthetic analogs of atrial peptides and more particularly to synthetic peptide compounds which find use as diuretics, natriuretics and/or vasodilators, or as intermediates for or modulators of such useful compounds, together with methods for their production and use.

BACKGROUND ART

Most multi-cellular organisms are organized into tissues and organs which perform specialized functions. Thus, a system has evolved to transport and circulate materials between them. In higher animals, including mammals, this circulatory system is closed, in order to improve the efficiency of transport. The flow of blood fluid through this closed cardiovascular system requires that the fluid be maintained under pressure and the regulation of the systemic arterial blood pressure requires a complex interaction of numerous factors including, e.g., fluid volume and vascular elasticity and caliber.

The maintenance of normal extracellular fluid volume depends primarily on the excretion of sodium (natriuresis) and water (diuresis) by the kidneys. This is determined by (1) the rate at which plasma is filtered at the glomerulus (glomerular filtration rate, or GFR) and (2) the degree to which sodium is actively reabsorbed along the renal tubule (with water following passively). The latter process is in part regulated by the adrenal steroid hormone aldosterone. It has been long believed that, in addition to GFR and aldosterone, there must be a "third factor" which also regulates sodium reabsorption. It is now apparent that many of the phenomena which required the postulation of a "third factor" can be explained by the effects of physical forces (e.g. blood pressure, red blood cell concentration and plasma viscosity) on sodium reabsorption. Nonetheless, the search continues for a "natriuretic hormone" which might modulate tubular reabsorption.

A natriuretic effect has been demonstrated by crude extracts of rat atrial tissue but not ventricular tissue. De Bold, A. J. et al., Life Sciences, 28:89–94 (1981), Garcia, R., Experientia, 38:1071–73 (1982), Currie, M. G. et al., Science 221:71–73 (1983). Various peptides with diuretic and natriuretic properties have been isolated from atrial tissue and sequenced. Flynn, T. G. et al., Biochem. Biophys. Res. Commun. 117:859–865 (1983), Currie, M. G. et al., Science 223:67–69 (1984), Kangawa, K. et al., Biochem. Biophys. Res. Commun. 118:131–139 (1984).

More recently, various seemingly related peptides have been isolated, sequenced and shown to have natriuretic, diuretic and vasorelaxant activity in varying degrees. U.S. Pat. No. 4,496,544; U.S. Pat. No. 4,508,712; Kangawa, K. et al., Biochem. Biophys. Res. Commun. 121(2):585–591 (1984); Kangawa, K. et al., Biochem. Biophys. Res. Commun. 119(3):933–940; Garcia R. et al., Biochem. Biophys. Res. Commun. 126(1):178–184 (1985); Katsube, N. et al.. Biochem. Biophys. Res. Commun. 128(1):325–330 (1985).

The existence of these atrial natriuretic factors strengthens the long-held suspicion that the heart, aside from its obvious influence on renal perfusion, plays an important role in regulating renal sodium and water excretion.

A number of clinically important disease states are characterized by abnormal fluid volume retention. Congestive heart failure, cirrhosis of the liver and the nephrotic syndrome each lead to excessive fluid accumulation on the venous side of the circulation, the presumed common mechanism being under-perfusion of the kidneys leading to a fall in GFR. In addition the reduced renal perfusion stimulates excessive secretion of renin, a proteolytic enzyme whose action in the circulation leads to the formation of angiotensin. Angiotensin is a powerful constrictor of arterioles (which helps to maintain arterial pressure) and also stimulates release of the sodium-retaining hormone aldosterone by the adrenal gland (which further worsens fluid retention). These mechanisms do not, however, fully account for the fluid retention of the so-called "edematous states", and additional factors are likely to be involved. One important possibility is that a relative or absolute deficiency of atrial natriuretic factor might contribute to the fluid retention.

An increase in extracellular fluid volume is also thought to contribute to the development of hypertension in many instances. Hypertension, or chronically elevated blood pressure, is one of the major causes of illness and death worldwide. It is estimated that more than 20 million Americans suffer from this disease whose complications include heart failure, heart attack, stroke and kidney failure. The major observed hemodynamic abnormality in chronic hypertension is increased resistance to the flow of blood through the arterioles. The mechanisms which lead to this increased "peripheral resistance" are, however, incompletely understood. In some cases inappropriate activity of the renin-angiotensin system or sympathetic nervous system may lead to excessive constriction of the arterioles; by "inappropriate" it is meant that the unknown signal(s) leading to this activity are not based upon a physiological need of the organism and thus lead to elevated blood pressure. In a substantial fraction of hypertensives however, inappropriate sodium and volume retention by the kidney is felt to either initiate or contribute to the elevated blood pressure. The responsible defect in kidney function and the mechanism whereby fluid retention leads to increased peripheral resistance are both unknown. It is certainly possible that deficiency of a natriuretic hormone could be responsible for these observations, particularly if the same substance also normally exerted a relaxant effect on arterioles.

Diuretic therapy is currently a mainstay in the treatment of hypertension, renal failure and the various edematous states (heart failure, etc.). Currently available pharmacological preparations have, however, several important limitations and undesirable effects. While their use may be directed at a specific abnormality (i.e. volume expansion), their multiple actions are undoubtedly not physiological, leading for instance to potassium depletion, increased retention of uric acid and abnormal glucose and lipid metabolism. In addition, all known diuretics profoundly stimulate the renin-angiotensin-aldosterone system, which counteracts their volume-depleting and blood pressure-lowering effects and leads to other unwanted effects. It would be desirable to provide a pharmacologically effective compound which can regulate blood pressure by providing a complete but controlled range of physiological responses.

However, the isolation of such compounds from atrial tissue is typically a cumbersome process and requires substantial substrate tissue to produce minute quantities of the compounds.

Furthermore, it is considered desirable to provide modifications to the native structures reported for these atrial natriuretic factors in order to isolate the regions of the peptides responsible for the distinct biological activities or regions important in the metabolism and clearance of the peptide. Having determined the appropriate units of activity, structural analogs can be created which preserve. e.g., natriuretic or diuretic activity while decreasing or eliminating vasorelaxant activity. Furthermore, shortened peptide sequences will provide active synthetic analogs which can be taken orally or delivered intranasally to provide the therapeutic benefits of the native compositions.

Shortened peptide sequences will also desirably be formulated to enhance their direct or indirect biological activity, resistance to degradation, biological half-life and to enable the chemosynthetic production of these compounds in a cost effective manner for clinical use.

DISCLOSURE OF THE INVENTION

It has been found that hypertension and various other edematous states can be effectively treated by the administration of synthetic analogs of native Atrial Natriuretic Peptides (ANP) which have been prepared in accordance with the present invention and which possess the natriuretic, diuretic and/or vasorelaxant activity of the native peptides in varying degrees.

Compounds of the present invention useful as natriuretics, diuretics, vasodilators and/or modulators of the renin-angiotensin-aldosterone system include such synthetic analogs of Atrial Natriuretic Peptides. The present analog peptide compounds are generally identified by the formula:

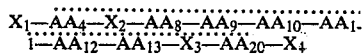
$X_1-AA_4-X_2-AA_8-AA_9-AA_{10}-AA_{11}-AA_{12}-AA_{13}-X_3-AA_{20}-X_4$ (I)

wherein:
AA$_4$ is a bond or a neutral amino acid residue, preferably C, [D—C], A, [D—A] or desAA$_4$;
AA$_8$ is a bond or a basic polar amino acid residue, preferably R, [D—R], K, [D—K] or desAA$_8$;
AA$_9$ and AA$_{12}$ are each the same or different neutral nonpolar amino acid residues, preferably where AA$_9$ is I, [D—I], M, [D—M] or V and AA$_{12}$ is I, [D—I] or [D—V];
AA$_{10}$ is an acidic polar amino acid residue, preferably D, [D—D] or E;
AA$_{11}$ is a basic polar amino acid residue, preferably R or [D—R];
AA$_{13}$ is a bond or a neutral polar amino acid residue, preferably G, A, [D—A], Aib or desAA$_{13}$;
AA$_{20}$ is a bond or a neutral amino acid residue, preferably C, [D—C], A, [D—A] or desAA$_{20}$;
X$_1$ is hydrogen, amido, acetyl, or additionally includes an amino acid, dipeptide, tripeptide or an oligopeptide of up to 125 amino acid residues, including Amino-terminal acetyl derivatives thereof;

X$_2$ is a bond, an amino acid or oligopeptide of up to 10, generally 5 and more usually 3 and preferably 2 or fewer amino acids;
X$_3$ is a bond, an amino acid or oligopeptide of up to approximately 10 residues, more usually 6 and preferably 5 or fewer; and
X$_4$ is hydroxyl, amido, or additionally includes an amino acid, dipeptide, tripeptide or an oligopeptide of up to 20 amino acid residues, including Carboxy-terminal amide derivatives thereof; and
including compounds having an optional bond, preferably a disulfide bond, joining the residues AA$_4$ and AA$_{20}$, when these residues are each independently C or [D—C]; and
wherein, for each amino acid residue or X$_n$ having amino acid residues or sequences of residues therein, each residue of the peptide can be the D-isomer or L-isomer; and
each residue having the capability of being substituted with a substituent group, preferably an organic group including any of hydrogen or an aliphatic, aromatic or alkaryl group of from one to ten, usually one to six carbon atoms, including groups having substitutions of three or less nitrogen, oxygen or sulfur atoms as amido, thio or oxy, including hydroxy, thiol and ethers, wherein the ether is usually an alkyl ether, generally of one carbon atom, e.g. methyl;
with the proviso that either: when X$_2$ is a tripeptide, X$_3$ is not a hexapeptide, or when X$_2$ is a tripeptide and X$_3$ is a hexapeptide, at least one of AA$_4$, AA$_8$, AA$_{13}$ AA$_{20}$ or is desAA$_n$.

Also provided in accordance with the invention are pharmaceutical compositions useful as natriuretics, diuretics, vasodilators and/or modulators of the renin-angiotensin-aldosterone system, which compositions containing the above-recited peptide compounds, including their amides and esters, and the nontoxic addition salts thereof, together with a pharmaceutically acceptable liquid, gel or solid carrier. Administration of therapeutically effective doses of these compositions can provide effective delivery of the above-recited biological activities to mammalian hosts.

Also provided in the present invention are methods for producing such compounds and compositions, and methods for using the compounds and compositions as therapeutic agents.

BRIEF DESCRIPTION OF THE DRAWINGS

FIG. 1 is a graph which depicts competitive displacement receptor binding of compounds of the present invention using cultured bovine aortic smooth muscle (BASM) cells; and FIG. 2 depicts the in vivo diuretic activities of selected compounds of the present invention in anesthetized rats, wherein FIG. 2A portrays the diuretic activity of the analog peptide identified as AP25, FIG. 2B portrays the diuretic activity of the analog peptide identified as AP20, FIG. 2C portrays the diuretic activity of the analog peptide identified as AP21, FIG. 2D portrays the diuretic activity of the analog peptide identified as AP37, FIG. 2E portrays the diuretic activity of the analog peptide identified as AP101, and FIG. 2F portrays the diuretic activity of the analog peptide identified as AP54.

BEST MODE FOR PRACTICING THE INVENTION

In accordance with the present invention novel Atrial Natriuretic Peptide (ANP) analog compounds are provided for the regulation of fluid volume and blood pressure in host organisms, in which one aspect of the invention provides ANP analog peptide compounds comprising the formula:

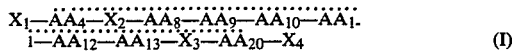

(I)

wherein:
- $AA_4$ is a bond or a neutral amino acid residue, preferably C, [D—C], A, [D—A] or $desAA_4$;
- $AA_8$ is a bond or a basic polar amino acid residue, preferably R, [D—R], K, [D—K] or $desAA_8$;
- $AA_9$ and $AA_{12}$ are each the same or different neutral nonpolar amino acid residues, preferably where $AA_9$ is I, [D—I], M, [D—M] or V and $AA_{12}$ is I, [D—I] or [D—V];
- $AA_{10}$ is an acidic polar amino acid residue, preferably D, [D—D] or E;
- $AA_{11}$ is a basic polar amino acid residue, preferably R or [D—R];
- $AA_{13}$ is a bond or a neutral polar amino acid residue, preferably G, A, [D—A], Aib or $desAA_{13}$;
- $AA_{20}$ is a bond or a neutral amino acid residue, preferably C, [D—C], A, [D—A] or $desAA_{20}$;
- $X_1$ is hydrogen, amido, acetyl, or additionally includes an amino acid, dipeptide, tripeptide or an oligopeptide of up to 125 amino acid residues, including Amino-terminal acetyl derivatives thereof;
- $X_2$ is a bond, an amino acid or oligopeptide of up to 10, generally 5 and more usually 3 and preferably 2 or fewer amino acids;
- $X_3$ is a bond, an amino acid or oligopeptide of up to approximately 10 residues, more usually 6 and preferably 5 or fewer; and
- $X_4$ is hydroxyl, amido, or additionally includes an amino acid, dipeptide, tripeptide or an oligopeptide of up to 20 amino acid residues, including Carboxyterminal amide derivatives thereof;

and including compounds having an optional bond, preferably a disulfide bond, joining the residues $AA_4$ and $AA_{20}$, as indicated by the broken line, when these residues are each independently C or [D—C]; and wherein, for each amino acid residue or $X_n$ having amino acid residues or sequences of residues therein, each residue of the peptide can be any of the D-isomer or L-isomer; and each residue having the capability of being substituted with a substituent group, preferably an organic group including any of hydrogen or an aliphatic, aromatic or alkaryl group of from one to ten, usually one to six carbon atoms, including groups having substitutions of three or less nitrogen, oxygen or sulfur atoms as amido, thio or oxy, including hydroxy, thiol and ethers, wherein the ether is usually an alkyl ether, generally of one carbon atom, e.g. methyl;

with the proviso that either: when $X_2$ is a tripeptide, $X_3$ is not a hexapeptide, or when $X_2$ is a tripeptide and $X_3$ is a hexapeptide, at least one of $AA_4$, $AA_8$, $AA_{13}$ or $AA_{20}$ is $desAA_n$.

Also included in the present invention are ANP analog compounds having the general formula:

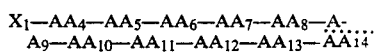
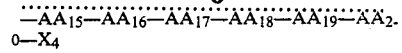

(II)

wherein
- $AA_4$ is a bond or a neutral amino acid residue, preferably C, [D—C], A, [D—A] or $desAA_4$;
- $AA_5$, $AA_{14}$ and $AA_{18}$ are each a bond or the same or different neutral amino acid residues, preferably where $AA_5$ is F, [D—F], A, [D—A] or $desAA_5$, $AA_{14}$ is A, [D—A], Aib or $desAA_{14}$ and $AA_{18}$ is L or $desAA_{18}$;
- $AA_6$, $AA_7$, $AA_{13}$, $AA_{15}$, $AA_{16}$, $AA_{17}$ and $AA_{19}$ are each a bond or the same or different neutral amino acid residues, preferably where $AA_6$ is G, A, [D—A], [D—S], [D—L], [D—V], Aib or $desAA_6$, $AA_7$ is G, A, [D—A] or $desAA_7$, $AA_{13}$ is G, [D—A], Aib or $desAA_{13}$, $AA_{15}$ is Q, A or $desAA_{15}$, $AA_{16}$ is S or $desAA_{16}$, $AA_{17}$ is G, A, [D—A] or $desAA_{17}$, and $AA_{19}$ is G, A, [D—A] or $desAA_{19}$;
- $AA_8$ is a bond or a basic polar amino acid residue, preferably R, [D—R], K or [D—K];
- $AA_9$, $AA_{12}$, are each the same or different neutral nonpolar amino acid residues, preferably where $AA_9$ is I, [D—I], M or [D—M], or [D—V] and $AA_{12}$ is I, [D—I] or [D—V];
- $AA_{10}$ is an acidic polar amino acid residue, preferably D, [D—D] or E;
- $AA_{11}$ is a basic polar amino acid residue, preferably R or [D—R];
- $AA_{20}$ is a bond or a neutral amino acid residue, preferably C, [D—C], A, [D—A] or $desAA_{20}$;
- $X_1$ is as previously defined, preferably an amino acid or oligopeptide of up to 6 amino acids and desirably an oligopeptide selected from the group consisting of S—L—R—R—S—S, L—R—R—S—S, R—R—S—S, R—S—S, S—S, S, R, Y and $desX_1$, including the Amino-terminal protonated, acetylated and amidated forms thereof;
- $X_4$ is as previously defined; and
- the residues $AA_4$ and $AA_{20}$ disclosed above are optionally but desirably joined by a bond, preferably a disulfide bond, when these residues are each independently C or [D—C];

with the proviso that: least one of $AA_4$ through or $AA_{13}$ through $AA_{20}$ is $desAA_n$.

Also included in the present invention are ANP analog compounds having the general formula:

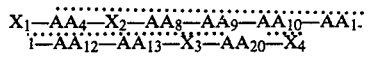

(III)

wherein:
- $AA_4$ is a bond or a neutral amino acid residue, preferably C, [D—C], A, [D—A] or $desAA_4$;
- $AA_8$ is a bond or a basic polar amino acid residue, preferably R, [D—R], K, [D—K] or $desAA_8$;
- $AA_9$ and $AA_{12}$ are each the same or different neutral nonpolar amino acid residues, preferably where $AA_9$ is I, [D—I], M, [D—M]or [D—V] and $AA_{12}$ is I, [D—I] or [D—V];
- $AA_{10}$ is an acidic polar amino acid residue, preferably D, [D—D] or E;
- $AA_{11}$ is a basic polar amino acid residue, preferably R or [D—R];
- $AA_{13}$ is a bond or a neutral polar amino acid residue, preferably G, A, [D—A], Aib or $desAA_3$;

AA₂₀ is a bond or a neutral amino acid residue, preferably C, [D—C], A, [D—A] or desAA₂₀;

X₁ is hydrogen, amido, acetyl, or additionally includes an amino acid, dipeptide, tripeptide or an oligopeptide of up to 125 amino acid residues, including N-acetyl derivatives thereof;

X₂ is a bond, an amino acid or an oligopeptide of up to 10, generally 5 and more usually 3 amino acids;

X₃ is a bond, an amino acid or an oligopeptide of up to approximately 10 residues, more usually 6 and preferably 5 or fewer; and X₄ is hydroxyl, amido, or an amino acid, dipeptide, tripeptide or an oligopeptide of up to 20 amino acid residues, including Carboxy-terminal amide derivatives thereof;

including compounds having a disulfide bond joining the cysteine residues, as indicated; and including the physiologically acceptable salts, amides and esters thereof;

with the proviso that either: when X₂ is a tripeptide, X₃ is not a hexapeptide, or when X₂ is a tripeptide and X₃ is a hexapeptide, at least one of AA₄, AA₁₃ or AA₂₀ is desAA$_n$.

Neutral amino acid residues can be approximately sub-divided into polar and nonpolar classes. Neutral nonpolar amino acid residues are taken to mean those residues with hydrophobic side groups at physiologic pH values, generally aliphatic or aromatic hydrocarbons of from zero to ten, usually one to six carbon atoms, which may be substituted with two or less nitrogen, oxygen or sulfur atoms, including such amino acids as Alanine (A), Aminoisobutyric Acid (Aib), Valine (V), Leucine (L), Isoleucine (I), Proline (P), Methionine (M), Phenylalanine (F) and Tryptophan (W).

Neutral polar amino acid residues are taken to mean those residues with hydrophilic, uncharged side groups at physiologic pH values, including such amino acids as Glycine (G), Serine (S), Threonine (T), Cysteine (C), Tyrosine (Y), Asparagine (N) and Glutamine (Q).

Acidic polar amino acid residues are taken to mean those residues with hydrophilic, negatively charged side groups at physiologic pH values, including such amino acids as Aspartic acid (D) and Glutamic acid (E).

Basic polar amino acid residues are taken to mean those residues with hydrophilic, positively charged side groups at physiologic pH values, including such amino acids as Lysine (K), Arginine (R) and Histidine (H).

Generally preferred embodiments of the present invention include compounds identified by the following formula:

$$X_1—AA_4—X_2—AA_8—AA_9—AA_{10}—AA_{11}—AA_{12}—AA_{13}—X_3—AA_{20}—X_4 \quad (IV)$$

wherein:

AA₄ is a bond or a neutral amino acid residue, preferably C, [D—C], A, [D—A] or desAA₄;

AA₈ is a bond or a basic polar amino acid residue, preferably R, [D—R], K, [D—K] or desAA₈;

AA₉ and AA₁₂ are each the same or different neutral nonpolar amino acid residues, preferably where AA₉ is I, [D—I], M, [D—M] or [D—V] and AA₁₂ is I, [D—I] or [D—V];

AA₁₀ is an acidic polar amino acid residue, preferably D, [D—D] or E;

AA₁₁ is a basic polar amino acid residue, preferably R or [D—R];

AA₁₃ is a bond or a neutral polar amino acid residue, preferably G, [D—A], Aib or desAA₁₃;

AA₂₀ is a bond or a neutral amino acid residue, preferably C, [D—C], A, [D—A] or desAA₂₀;

and wherein X₁, X₂, X₃ and X₄ are as previously defined, desirably where:

Each X₁ is independently selected from the group consisting of S—L—R—R—S—S, L—R—R—S—S, R—R—S—S, R—S—S, S—S, S, R, Y and desX₁, and including the Amino-terminal Acetyl and Amido forms thereof; each X₂ is independently selected from the group consisting of F—G—G, F—G—A, F—A—G, F—[D—A]—G, F—[D—S]—G, F—[D—L]—G, F—[D—V]—G, [D—F]—G—G, [D—A]—G—G, F—G—[D—A], F—Aib—G, A—G—G, F—G, G—G, G and desX₂;

each X₃ is independently selected from the group consisting of A—Q—S—G—L—G, A—Q—S—G—L, A—Q—S—G, A—Q—S, A—Q, A, [D—A], Aib and desX₃; and each X₄ is independently selected from the group consisting of N—S—F—R—Y, N—S—F—R, N—S—F, N—S, N, and desX₄, and including the Carboxy-terminal amide derivatives thereof, with the proviso that either: when X₂ is a tripeptide, X₃ is not a hexapeptide, or when X₂ is a tripeptide and X₃ is a hexapeptide, at least one of AA₄, AA₈, AA₁₃ or AA₂₀ is desAA$_n$; and wherein the cysteine residues are desirably joined by a disulfide bond.

Certain presently preferred embodiments included in the above formula include, for example, without showing any disulfide bond:

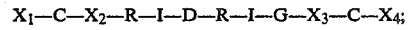

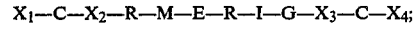

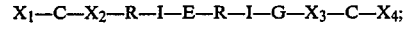

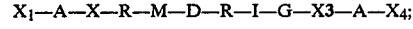

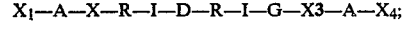

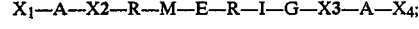

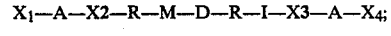

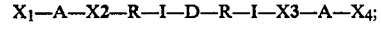

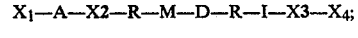

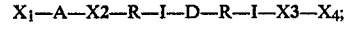

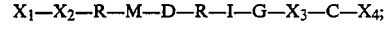

wherein each specified amino acid residue can be either the D- or L-isomer and the cysteine residues are optionally joined by a disulfide bond; and each X₁ is independently selected from the group consisting of S—L—R—R—S—S, L—R—R—

S—S, R—R—S—S, R—S—S, S, R, Y and desX$_1$, and including the Amino-terminal Acetyl, Hydro or Amido forms thereof;

each X$_2$ is independently selected from the group consisting of F—G—G, F—G—A, F—A—G, F—[D—A]—G, F—[D—S]—G, F—[D—L]—G, F—[D—V]—G, [D—F]—G—G, [D—A]—G—G, F—G—[D—A], F—Aib—G, A—G—G, F—G, G—G, G and desX$_2$;

each X$_3$ is independently selected from the group consisting of A—Q—S—G—L—G, A—Q—S—G—L, A—Q—S—G, A—Q—S, A—Q, A, [D—A], Aib and desX$_3$;

each X$_4$ is independently selected from the group consisting of N—S—F—R—Y, N—S—F—R, N—S—F, and desX$_4$, and including the Carboxy-terminal Hydroxyl or Amido forms thereof;

generally with the proviso that: when X$_2$ is a tripeptide, X$_3$ is not a hexapeptide.

The nomenclature used to describe ANP analog compounds of the present invention follows the conventional practice wherein the amino group is presented to the left and the carboxy group to the right of each amino acid residue. In the formulae representing selected specific embodiments of the present invention, the Amino- and Carboxy-terminal groups, although not specifically shown, will be understood to be in the form they would assume at physiologic pH values, unless otherwise specified. In the amino acid structure formulae, each residue is generally represented by a single letter designation, corresponding to the trivial name of the amino acid, in accordance with the following schedule:

| Amino Acid | One-letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The non-protein amino acid Aminoisobuytric Acid is represented by the 3-letter designation: Aib.

In the present application, the L-form of any amino acid residue having an optical isomer is intended unless otherwise expressly indicated, e.g., by the symbol "[D—AA$_n$]".

Compounds within the scope of the present invention can also be obtained by modifying the above recited formulae in numerous ways while preserving the activity of the ANP analog compounds thus obtained. For example, while the amino acids of these compounds are normally in the natural L form, one or more, usually two or less and preferably one amino acid may be replaced with the optical isomer D form, or a D,L- racemic mixture can be provided in the molecules comprising the peptide compound Amino acid residues contained within the compounds, and particularly at the Carboxy- or Amino-terminus, can also be modified by amidation, acetylation or substituted with other chemical groups which can, for example, change the solubility of the compounds without effecting their activity. In particular, it has been discovered that amide analogs of Atrial Natriuretic Peptides are particularly potent and therefore preferred embodiments of the present invention. For example, the Carboxy-terminal residue will have a carbonyl carbon which has been substituted with an amino group to form a Carboxy-terminal amido group. In general, the nitrogen of the amido group, covalently bound to the carbonyl carbon, will have two substituent groups, each of which can be hydrogen, alkyl, a benzylic group (substituted or unsubstituted), and any one of which can be a nitrogen containing moiety such as hydrazide and the other can be hydrogen, or either group can be a basic or neutral dipeptide and the other can be hydrogen or an alkyl group. Representative among such amido groups are: —NH$_2$, —NHCH$_3$, —N(CH$_3$)$_2$, among others.

In forming amidated analogs of the present invention, the analog compound can be synthesized directly, for example using BOC-AA-pMBHA-Resin or Boc-AA-BHA-Resin, wherein AA is the selected Carboxy-terminal amino acid of the desired analog compound as described in further detail below. Alternatively, the analog compounds of the present invention can be chemically amidated subsequent to peptide synthesis using means well known to the art, or enzymatically amidated.

Alternatively, certain amino acid residues contained within the disclosed compounds, and particularly at the Amino-terminus, can also be modified by deamination, in order to provide resistance to degradation in the host by endogenous peptidase enzyme claevage. Such deamination can be accomplished in the synthesized compound, for example, by employing L Amino Acid Oxidase (EC 1.4.3.2, derived from the venom of, e.g., *Crolatus atrox*) or D Amino Acid Oxidase (EC 1.4.3.3, derived from, e.g., porcine kidney), which are available commercially (Sigma Chemical Co., St. Louis, Mo.).

Preferably, deamination can by effectively accomplished by selecting the appropriate α-keto acid as an alternative to the desired Amino-terminal amino acid residue. For example, the amino acid residues arginine, serine, leucine, cysteine, alanine, phenylalanine and glycine can be replaced with the alternative α-keto acids 5-Guanidino pentanoic acid, 3-Hydroxy propionic acid, 4-Methyl pentanoic acid, 3-Mercapto propionic acid, Propionic acid, Hydrocinnamic acid and Acetic acid, respectively. Most α-keto acids which correspond to the amino acid residues employed in the present invention are available commercially, e.g., from Aldrich Chemical Co., Inc., Milwaukee, Wis. The desired α-keto acid can also be synthesized by means well known to those having ordinary skill in the art of chemical synthesis.

In addition, one or more amino acid residues can be replaced by functionally equivalent residues; for example basic polar amino acids can be replaced with other basic polar amino acids and acidic polar amino acids can be replaced with other acidic polar amino acids.

Certain cyclic analogs of the present invention can be provided by including a disulfide bridge between the sulfhydryl groups of cysteine residues to form a cystine residue. Alternatively, the cysteine residues, or equivalent residues, can be bridged by replacing the disulfide bridge with an equivalent bond or linking group such as, for example, —CH$_2$—. The replacement of a sulfhydryl group on the cysteine residue with an alternative group will effectively replace the cysteine residue with an alternative amino acid. For example, replacing the sulfhydryl group with a —CH$_2$— group will convert the residue to α-amino butyric acid.

Additional ANP analog compounds within the scope of the invention are provided in linear form wherein the bridging bond is not present and is replaced by hydrogen, while preserving substantially the same biological activity. For example, as is disclosed in further detail below, one or both cysteine residues can be replaced, e.g., by alanine residues, or deleted, to provide preferred linear analog peptides in accordance with the present invention.

The ANP analog compounds of the present invention can also be modified by extending, decreasing or substituting in the compounds' amino acid sequence, e.g., by the addition or deletion of amino acids or oligopeptides on either the Amino-terminal or Carboxy-terminal end, or both, of the sequences disclosed above. Particularly, X$_4$ can be amide or an amino acid or oligopeptide of not more than about 20, more usually 8, and desirably 5 or less amino acids and X$_1$ can be N-acetyl or an amino acid or oligopeptide of not more than about 125, and desirably up to about 100 amino acids, provided the modifications do not adversely effect all of the natriuretic, diuretic and/or vasorelaxant activities of the subject compounds.

The present ANP analog compounds can also be modified by altering the order in which certain residues are provided in the amino acid sequence of the compound. In particular, it will be readily appreciated that, while certain sequences of oligopeptides are provided as preferred embodiments for the analog peptide regions designated X$_n$ where n=1, 2, 3 or 4, these regions, and the preferred sequences of amino acid residues contained therein, have been shown not to be essential to the biological activity of the compounds. Therefore, the amino acid sequence of the instant peptides can be altered so that, rather than eliminating amino acid residues sequentially from the Amino- or Carboxy-terminal ends, substitutions, rearrangements and deletions can be made at any location in the aforementioned X$_n$ regions, while remaining within the scope of the present invention. Thus, the number of alternative embodiments contained within the previously disclosed formulae I, II, III and IV are governed, in part, by the mathematical laws of permutations and combinations.

Furthermore, compounds of the present invention can be mixed with, bonded to, or conjugated or complexed with compounds having the same or a complementary range of biologic activities to obtain the benefits of the present invention.

Compounds within the scope of the present invention can be synthesized chemically by means well-known in the art such as, e.g., solid phase peptide synthesis. The synthesis is commenced from the Carboxy-terminal end of the peptide using an alpha-amino protected amino acid. t-Butyloxycarbonyl (Boc) protective groups can be used for all amino groups even though other protective groups are suitable. For example, Boc—N—OH, Boc—S—OH, Boc—F—OH, Boc—R—OH or Boc—Y—OH (i.e., selected ANP analog Carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart et al., Solid-Phase Peptide Synthesis, W. H. Freeman Co., San Francisco (1969) and Merrifield, J. Am. Chem. Soc. 85:2149–2154 (1963). These and other methods of peptide synthesis are also exemplified by U.S. Pat. Nos. 3,862,925, 3,842,067, 3,972,859 and 4,105,602.

In the synthesis of those compounds which include a deaminated Amino-terminal amino acid residue, the appropriate α-keto acid can generally be added without employing the protecting groups ordinarily used with amino acid residues. However, succinic acid and glutaric acid (the α-keto acids corresponding to aspartic acid and glutamic acid, respectively) will generally be incorporated by employing the ½ benzyl derivative of the α-keto acid.

Conveniently, compounds may be synthesized using manual techniques or automatically employing, for example, an Applied BioSystems 430A Peptide Synthesizer (Foster City, Calif.) or a Biosearch SAM II automatic peptide synthesizer (Biosearch, Inc. San Rafael, Calif.) following the instructions provided in the instruction manual supplied by the manufacturer.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

Alternatively, compounds of the present invention can be produced by expression of recombinant DNA constructs prepared in accordance with well-known methods. Such production can be desirable to provide large quantities or alternative embodiments of such compounds.

More particularly, modifications in the amino acid sequence of the various forms of ANP analog compounds to provide alternative embodiments of the present invention can be effected by various changes in the nucleotide sequence of the cloned or synthetic structural gene used to direct the synthesis of the compounds. Included within such modification of the DNA sequence are the replacement of various codons with other codons which, due to the degeneracy of the genetic code, direct the synthesis of the same amino acid. In addition, by codon substitution, one or more amino acid residues can be replaced by functionally equivalent residues, as disclosed above.

Compounds of the present invention are shown to have natriuretic, diuretic and hypotensive activity in the intact mammal. Furthermore, compounds of the present invention including synthetic compounds, may possess vasorelaxant activity or inhibit the release of aldosterone.

Compounds of the present invention, in straight chain or cyclic ring form, which are shown to have the above recited physiological effects can find use in numerous therapeutical applications such as, e.g., inducing natriuresis, diuresis, and vasodilatation. Thus these compounds, and compositions containing them, can find use as therapeutic agents in the treatment of various edematous states such as, for example, congestive heart failure, nephrotic syndrome and hepatic cirrhosis, in addition to hypertension and renal failure due to ineffective renal perfusion or reduced glomerular filtration rate.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 0.01 to 100 $\mu$g/kg, more usually 0.1 to 10 $\mu$g/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiological tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%–95% of active ingredient, preferably 25%–70%.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to alternate receptors, stimulating receptor turnover, or providing alternate substrates for degradative enzyme or receptor activity and thus inhibiting these enzymes or receptors. When employed in this manner, such compounds can be delivered as admixtures with other active compounds or can be delivered separately, for example, in their own carriers.

Compounds of the present invention can also be used for preparing antisera for use in immunoassays employing labelled reagents, usually antibodies. Conveniently, the polypeptides can be conjugated to an antigen by means of dialdehydes, particularly from 4 to 6 carbon atoms and aliphatic, or carbodiimide. These compounds and immunologic reagents may be labelled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The following examples are provided by way of illustration, rather than implying any limitation of the subject invention.

EXPERIMENTAL

In the experimental disclosure which follows, the amino acid sequence of chemically synthesized ANP analog compounds are numbered from the Amino-terminal arginine residue corresponding to the arginine residue found at position 1 in the native rat-derived Atrial Natriuretic Peptide sequence disclosed in Atlas, S. et al., Nature 309:717–719 (1984).

I. Chemical Synthesis of Atrial Natriuretic Peptide Analog Compounds

A. Synthesis Procedures

Compounds of the present invention having the general formula:

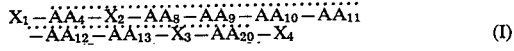

(I)

wherein:
- AA$_4$ is a bond or a neutral amino acid residue, preferably C, [D—C], A, [D—A] or desAA$_4$;
- AA$_8$ is a bond or a basic polar amino acid residue, preferably R, [D—R], K, [D—K] or desAA$_8$;
- AA$_9$ and AA$_{12}$ are each the same or different neutral nonpolar amino acid residues, preferably where AA$_9$ is I, [D—I], M, [D—M] or [D—V] and AA$_{12}$ is I, [D—I] or [D—V];

$AA_{10}$ is an acidic polar amino acid residue, preferably D, [D—D] or E;

$AA_{11}$ is a basic polar amino acid residue, preferably R or [D—R];

$AA_{13}$ is a bond or a neutral polar amino acid residue, preferably G, [D—A], Aib or desAA13;

$AA_{20}$ is a bond or a neutral amino acid residue, preferably C, [D—C], A, [D—A] or desAA20;

$X_1$ is hydrogen, amido, acetyl, or additionally includes an amino acid, dipeptide, tripeptide or an oligopeptide of up to 125 amino acid residues, including Amino-terminal acetyl derivatives thereof;

$X_2$ is a bond, or an amino acid or oligopeptide of up to 10, generally 5 and more usually 3 and preferably 2 or fewer amino acids;

$X_3$ is a bond, or an amino acid or oligopeptide of up to approximately 10 residues, more usually 6 and preferably 5 or fewer; and $X_4$ is hydroxyl, amido, or additionally includes an amino acid, dipeptide, tripeptide or an oligopeptide of up to 20 amino acid residues, including Carboxy-terminal amide derivatives thereof;

and including compounds having an optional bond, preferably a disulfide bond, joining the residues $AA_4$ and $AA_{20}$ when these residues are each independently C or [D—C]; and wherein each $X_n$ is an amino acid residue, or sequence of residues, each having the general formula previously defined, and including the physiologically acceptable salts, amides and esters thereof, with the proviso that either when $X_2$ is a tripeptide, $X_3$ is not a hexapeptide, or when $X_2$ is a tripeptide and $X_3$ is a hexapeptide, at least one of $AA_4$, $AA_8$, $AA_{13}$ or $AA_{20}$ is desAA$_n$; have been prepared in order to illustrate the present invention.

In particular, ANP analog compounds having the general formula:

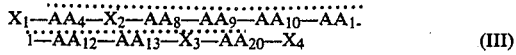 (III)

wherein:

$AA_4$ is a bond or a neutral amino acid residue, preferably C, [D—C], A, [D—A] or desAA4;

$AA_8$ is a bond or a basic polar amino acid residue, preferably R, [D—R], K, [D—K] or desAA8;

$AA_9$ and $AA_{12}$ are each the same or different neutral nonpolar amino acid residues, preferably where $AA_9$ is I, [D—I], M, [D—M] or [D—V] and $AA_{12}$ is I, [D—I] or [D—V];

$AA_{10}$ is an acidic polar amino acid residue, preferably D, [D—D] or E;

$AA_{11}$ is a basic polar amino acid residue, preferably R or [D—R];

$AA_{13}$ is a bond or a neutral polar amino acid residue, preferably G, [D—A], Aib or desAA13;

$AA_{20}$ is a bond or a neutral amino acid residue, preferably C, [D—C], A, [D—A] or desAA20;

and wherein $X_1$, $X_2$, $X_3$ and $X_4$ are as previously defined, desirably where:

Each $X_1$ is independently selected from the group consisting of S—L—R—R—S—S, L—R'—R—S—S, R—R—S—S, R—S—S, S—S, S, R, Y and desX1, and including the Amino-terminal Acetyl and Amido forms thereof;

each $X_2$ is independently selected from the group consisting of F—G—G, F—G—A, F—A—G, F—[D—A]—G, F—[D—S]—G, F—[D—L]—G, F—[D—V]—G, [D—F]—G—G, [D—A]—G—G, F—G—[D—A], F—Aib—G, A—G—G, F—G, G—G, G and desX2;

each $X_3$ is independently selected from the group consisting of A—Q—S—G—L—G, A—Q—S—G—L, A—Q—S—G, A—Q—S, A—Q, A, [D—A], Aib and desX3; and each $X_4$ is independently selected from the group consisting of N—S—F—R—Y, N—S—F—R, N—S—F, N—S, N, and desX4, and including the Carboxy-terminal amide derivatives thereof, with the proviso that either: when $X_2$ is a tripeptide, $X_3$ is not a hexapeptide, or when $X_2$ is a tripeptide and $X_3$ is a hexapeptide, at least one of $AA_4$, $AA_8$, $AA_{13}$ or $AA_{20}$ is desAA$_n$; and wherein the cysteine residues are desirably joined by a disulfide bond, were synthesized by solid-phase techniques. Syntheses were performed manually or, alternatively, on an Applied BioSystems 430A Peptide Synthesizer (Foster City, Calif.) or a Biosearch SAM II automated peptide synthesizer (Biosearch, San Rafael, Calif.) using t-Boc amino acids in accordance with the instructions of the manufacturer.

In accordance with the above description, the following procedures were used for the chemical synthesis of novel ANP analog compounds.

Procedure A

Preparation of Boc-AA$_1$ . . . AA$_{n-1}$-AA$_n$-Resin Hydroxymethyl Polystyrene Ester One gram of selected Boc-AA$_n$-O-Polystyrene-Resin (0.2–0.6 mmole/g resin) (obtainable from, e.g., Peninsula Labs, Inc.) is treated according to schedule A for incorporation of the Boc-AA$_{n-1}$-OH.

Schedule A (1) Wash 3x with dichloromethane ($CH_2Cl_2$);
(2) Treat for 1 min. with TFA:$CH_2Cl_2$:ethane dithiol (EDT) (45:50:5 by volume);
(3) Treat for 20 min. with TFA:$CH_2Cl_2$:EDT (45:50:5) by volume;
(4) Wash 3x with $CH_2Cl_2$;
(5) Treat 2x for 1 min. 10% (V/V) Diisopropylethylamine (DIPEA) in $CH_2Cl_2$;
(6) Wash 2x with $CH_2Cl_2$;
(7) Wash 2x with methanol (MeOH);
(8) Repeat (5–7) once;
(9) Wash 3x with $CH_2Cl_2$;
(10) Add 1–6 equivalents of preformed symmetrical anhydride of the suitably protected Boc-amino acid dissolved in $CH_2Cl_2$ or dimethyl formamide (DMF)/$CH_2Cl_2$ (50:50 volume) (Boc-N-OH, Boc-Q-OH and Boc-R(TOS)-OH were coupled as active esters using N-hydroxybenzotriazole);
(11) Wash 2x with $CH_2Cl_2$;
(12) Wash 2x with 10% DIPEA;
(13) Wash 2x with $CH_2Cl_2$;
(14) Wash 2x with MeOH;
(15) Wash 2x with $CH_2Cl_2$;
(16) Repeat steps (11–15) once;
(17) Test by ninhydrin reaction according to Kaiser et al., Anal. Biochem. 34:595 (1970). If the coupling reaction was incomplete, repeat steps (10–16) or, alternatively, cap synthesis using N-acetyl imidazole (0.30M in DMF) or an excess of acetic anhydride in $CH_2Cl_2$.

PROCEDURE B

Preparation of Boc-AA$_n$-p-Methylbenzhydrylamine resin

The selected Boc-AA$_n$-OH is attached to a p-Methylbenzhydrylamine (pMBHA) resin via N,N'-dicyclohexylcarbodiimide, as described below.

Schedule B (1) Wash the p-MBHA.HCl resin;
(2) Wash the resin 2x with 10% (V/V) DIPEA in CH$_2$Cl$_2$;
(3) Wash 2x with CH$_2$Cl$_2$;
(4) Wash 2x with MeOH;
(5) Wash 2x with CH$_2$Cl$_2$;
(6) Add 1-6 equivalents of preformed symmetrical anhydride of the suitably protected Boc-amino acid dissolved in CH$_2$Cl$_2$, with reaction time of 0.5-24 hrs.

Unreacted amino groups are acetylated with 0.30M N-acetylimidazole:DMF, or acetic anhydride:CH$_2$Cl$_2$.

The following examples demonstrate the chemical synthesis of representative analog peptide compounds (identified as AP#) which illustrate certain aspects of the present invention.

EXAMPLE 1

\* AP1

R—S—S—C—F—G—G—R—I—D—R—I-
—G—A—Q—S—G—C—N—S—F—R—Y

One gm of Boc-Y(2BrZ)-O-Resin (0.54 meq/gm, Peninsula Labs Inc., Belmont, Calif.) was subjected to procedure A with the required sequence of amino acids (introduced in order as Boc—R(Tos)—OH, Boc—F—OH, Boc—S(Bzl)—OH, Boc—N—OH, Boc—C(-4—CH$_3$Bzl)—OH, Boc—G—OH, Boc—S(Bzl)—OH, Boc—Q—OH, Boc—A—OH, Boc—G—OH, Boc—I-—OH.½H$_2$O, Boc—R(Tos)—OH, Boc—D(OBzl)—OH, Boc—I—OH.½H$_2$O, Boc—R(Tos)—OH, Boc—G—OH, Boc—G—OH, Boc—F—OH, Boc—C(4—CH$_3$Bzl)—OH, Boc—S—(Bzl)—OH, Boc—S—(Bzl)—OH, Boc—R(Tos)—OH). The protected peptidyl resin was treated with TFA:CH$_2$Cl$_2$:EDT (45:50:5 v/v/v) for 1 min., then 20 min. and washed 3 times with CH$_2$Cl$_2$ and 2 times with MeOH to give the TFA salt of the peptidyl resin, and dried in vacuo.

The peptidyl resin was then suspended in anhydrous hydrogen fluoride (HF) containing 10% anisole, 2% ethyl methyl sulfide for 30 min. at −10° C., and 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once with diethyl ether. The peptide was extracted from the mixture with 2.0M acetic acid, diluted with H$_2$O and lyophilized, to give the unoxidized sulfhydryl peptide.

The crude peptide was dissolved in deoxygenated 0.01M ammonium acetate (NH$_4$OAc), pH 7.9, to 0.5 mg/ml and then oxidized by dropwise addition of a slight excess of 0.01M potassium ferricyanide (KCN) solution, stirred 20 minutes and adjusted to pH 5 with acetic acid. The peptide solution was treated with DOWEX AG3X4 anion exchange resin, filtered, diluted with H$_2$O and lyophilized to give the crude cyclized peptide.

Purification of the peptide was achieved by desalting on Sephadex® G-25F (Pharmacia Fine Chemicals) using 0.5M AcOH as eluant, followed by ion exchange chromatography on CM-Sepharose® (Pharmacia Fine Chemicals) or CM-cellulose (Whatman) using an elution gradient generated by addition of 300 mM NH$_4$OAc, pH6.5, to a solution of 10 mM NH$_4$OAc, pH 4.5. Fractions were collected having a minimum 97% purity, as judged by reversed phase HPLC, then pooled and lyophilized from H$_2$O several times to yield the purified AP1 acetate salt.

EXAMPLE 2

\* AP2

R—S—S—C—G—R—I—D—R—I-
—G—A—Q—S—G—C—N—S—F—R—Y 1 gm of Boc—Y(2BrZ)—O—Resin (0.54 meq/gm, Peninsula Labs Inc., Belmont, Calif.) was subjected to procedure A with the required sequence of amino acids (introduced in order as Boc—R(Tos)—OH, Boc—F—OH, Boc—S(Bzl)—OH, Boc—N—OH, Boc—C(-4—CH$_3$Bzl)—OH, Boc—G—OH, Boc—S(Bzl)—OH, Boc—Q—OH, Boc—A—OH, Boc—G—OH, Boc—I-—OH.½H$_2$O, Boc—R(Tos)—OH, Boc—D(OBzl)—OH, Boc—I—OH.½H$_2$O, Boc—R(Tos)—OH, Boc—G—OH, Boc—C(4CH$_3$Bzl)—OH, Boc—S(Bzl)—OH, Boc—S(Bzl)—OH, Boc—R(Tos)—OH). The protected peptidyl resin was treated with TFA:CH$_2$Cl$_2$:EDT (45:50:5 v/v/v) for 1 min., then 20 min. and washed 3 times with CH$_2$Cl$_2$, 2 times with MeOH and dried in vacuo to give the TFA salt of the peptidyl resin.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, twice with chloroform, and twice with diethyl ether. The peptide was extracted with 2.0M acetic acid and lyophilized, to give the unoxidized sulfhydryl peptide.

The crude peptide was dissolved in deoxygenated 0.01 M NH$_4$OAc, pH 7.9, to 0.5 mg/ml and then oxidized by dropwise addition of a slight excess of 0.01M KCN solution, stirred for 20 minutes and adjusted to pH 5 with acetic acid. The peptide solution was treated with DOWEX AG3X4 anion exchange resin, filtered, diluted with H$_2$O and lyophilized to give the crude cyclized peptide. Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH$_4$OAc, pH 6.5, to a solution of 10 mM NH$_4$OAc, pH 4.5. Fractions were collected having a minimum 97% purity, as judged by reversed phase HPLC, then pooled and lyophilized from H$_2$O several times to yield the purified AP2 acetate salt.

EXAMPLE 3

\* AP3

R—S—S—C—F—G—G—R—I—D—R—I-
—G—A—Q—S—C—N—S—F—R—Y

One gm of Boc—Y(2BrZ)—O—Resin (0.54 meq/gm, Peninsula Labs Inc., Belmont, Calif.) was subjected to procedure A with the required sequence of amino acids (introduced in order as Boc—R(Tos)—OH, Boc—F—OH, Boc—S(Bzl)—OH, Boc—N—OH, Boc—C(-

4—CH₃Bzl)—OH, Boc—S(Bzl)—OH, Boc—Q—OH, Boc—A—OH, Boc—G—OH, Boc—I—OH.½H₂O, Boc—R(Tos)—OH, Boc—D(OBzl)—OH, Boc—I—OH.½H₂O, Boc—R(Tos)—OH, Boc—G—OH, Boc—G—OH, Boc—F—OH, Boc—C(4CH₃Bzl)—OH, Boc—S(Bzl)—OH, Boc—S(Bzl)—OH, Boc—R(Tos)—OH). The protected peptidyl resin was treated with TFA:CH₂Cl₂:EDT (45:50:5 v/v/v) for 1 min., then 20 min. and washed 3 times with CH₂Cl₂ and twice with MeOH to give the TFA salt of the peptidyl resin and dried in vacuo.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once again with diethyl ether. The peptide was extracted from the mixture with 2.0M acetic acid, diluted with H₂O and lyophilized, to give the unoxidized sulfhydryl peptide.

The crude peptide was dissolved in deoxygenated 0.01M NH₄OAc, pH 8, to 0.5 mg/ml and then oxidized by dropwise addition of a slight excess of 0.01M KCN solution, stirred 20 minutes and adjusted to pH 5 with acetic acid. The peptide solution was treated with DOWEX AG3X4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc to a solution of 10 mM NH₄OAc, pH 4.5. Fractions were collected having a minimum 97% purity, as judged by reversed phase HPLC, then pooled and lyophilized from H₂O several times to yield the purified AP3 acetate salt.

EXAMPLE 4

* AP4

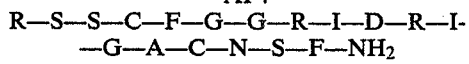

One gm of Boc-F-pMBHA resin, obtained using schedule B, was subjected to procedure A with the required sequence of amino acids (introduced in order as Boc—S(Bzl)—OH, Boc—N—OH, Boc—C(-4—CH₃Bzl)—OH, Boc—A—OH, Boc—G—OH, Boc—I—OH.½H₂O, Boc—R(Tos)—OH, Boc—D-(OBzl)—OH, Boc—I—OH.½H₂O, Boc—R(Tos)—OH, Boc—G—OH, Boc—G—OH, Boc—F—OH, Boc—C(4—CH₃Bzl)—OH, Boc—S(Bzl)—OH, Boc—S(Bzl)—OH, Boc—R(Tos)—OH). The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once again with diethyl ether. The peptide was extracted from the mixture with 2.0M acetic acid, diluted with H₂O and lyophilized, to give the unoxidized sulfhydryl peptide.

The crude peptide was dissolved in deoxygenated 0.01M NH₄OAc, pH 8, to 0.5 mg/ml and then oxidized by dropwise addition of a slight excess of 0.01M KCN, stirred for 20 minutes and adjusted to pH 5 with acetic acid. The peptide solution was treated with DOWEX AG3X4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc to a solution of 10 mM NH₄OAc, pH 4.5. Fractions were collected having a minimum 97% purity, as judged by reversed phase HPLC, then pooled and lyophilized from H₂O several times to yield the purified AP4 acetate salt.

Following the procedures outlined in Examples 1-4 (to produce analog peptides AP1-4) with appropriate modification, the following ANP analogs are synthesized (without showing any disulfide bonds):

| | | |
|---|---|---|
| | AP5 | S—L—R—R—S—S—C—F—G—G—R—I—D—R—I—G—A—Q—S—G—C—N—S—F—R—Y |
| | AP6 | S—L—R—R—S—S—C—F—G—G—R—I—D—R—I—G—A—C—N—S—F—R—Y |
| | AP7 | S—L—R—R—S—S—C—F—G—G—R—I—D—R—I—G—C—N—S—F—NH₂ |
| * | AP8 | S—L—R—R—S—S—C—G—R—I—D—R—I—G—A—Q—S—G—L—G—C—N—S—F—R—Y |
| * | AP9 | S—L—R—R—S—S—C—G—R—I—D—R—I—G—A—Q—S—G—L—G—C—N—S—F—NH₂ |
| | AP10 | S—L—R—R—S—S—C—F—G—G—R—I—D—R—I—G—A—C—NH₂ |
| * | AP11 | S—L—R—R—S—S—C—G—R—I—D—R—I—G—A—Q—S—G—L—G—C—NH₂ |
| | AP12 | L—R—R—S—S—C—F—G—G—R—I—D—R—I—G—A—C—N—S—F—R |
| * | AP13 | L—R—R—S—S—C—F—G—G—R—I—D—R—I—G—C—N—S—F—R—Y |
| * | AP14 | R—R—S—S—C—F—G—G—R—I—D—R—I—G—A—Q—S—G—C—N—S—F—R—Y |
| | AP15 | R—R—S—S—C—F—G—G—R—I—D—R—I—G—C—N—S—F—R—Y |
| | AP16 | R—R—S—S—C—G—R—I—D—R—I—G—A—Q—S—G—L—G—C—N—S—F—R—Y |
| | AP17 | R—R—S—S—C—F—G—G—R—I—D—R—I—G—A—Q—C—N—S—F—R—Y |
| * | AP18 | R—S—S—C—F—G—G—R—I—D—R—I—G—A—Q—S—G—L—C—N—S—F—R—Y |
| * | AP19 | R—S—S—C—F—G—G—R—I—D—R—I—G—A—Q—C—N—S—F—R—Y |
| * | AP20 | R—S—S—C—F—G—G—R—I—D—R—I—G—A—C—N—S—F—R—Y |
| * | AP21 | R—S—S—C—F—G—G—R—I—D—R—I—G—C—N—S—F—R—Y |
| * | AP22 | R—S—S—C—F—G—G—R—I—D—R—I—C—N—S—F—R—Y |

-continued

|   |       |                                                                   |
|---|-------|-------------------------------------------------------------------|
| * | AP23  | R—S—S—C—G—G—R—I—D—R—I—G—A—Q—S—G—L—G—C—N—S—F—R—Y |
| * | AP24  | R—S—S—C—G—R—I—D—R—I—G—A—Q—S—G—L—G—C—N—S—F—R—Y |
| * | AP25  | R—S—S—C—R—I—D—R—I—G—A—Q—S—G—L—G—C—N—S—F—R—Y |
|   | AP26  | S—S—C—F—G—G—R—I—D—R—I—G—A—C—N—S—F—NH₂ |
|   | AP27  | S—S—C—G—R—I—D—R—I—G—A—Q—S—G—L—G—C—N—S—F—R—Y |
|   | AP28  | S—S—C—R—I—D—R—I—G—A—Q—S—G—C—N—S—F—R—Y |
|   | AP29  | S—S—C—F—G—G—R—I—D—R—I—G—A—Q—C—N—S—F—R—Y |
|   | AP30  | S—C—F—G—G—R—I—D—R—I—G—A—C—N—S—F—R—Y |
|   | AP31  | S—C—G—R—I—D—R—I—G—A—Q—S—G—C—N—S—F—R—Y |
|   | AP32  | S—C—G—G—R—I—D—R—I—G—A—Q—S—G—C—N—S—F—NH₂ |
|   | AP33  | C—F—G—G—R—I—D—R—I—G—A—Q—S—G—C |
|   | AP34  | C—F—G—G—R—I—D—R—I—G—A—Q—S—C |
|   | AP35  | C—F—G—G—R—I—D—R—I—G—A—Q—C |
| * | AP36  | C—F—G—G—R—I—D—R—I—G—A—C |
| * | AP37  | C—F—G—G—R—I—D—R—I—G—A—C—NH₂ |
| * | AP38  | C—F—G—G—R—M—D—R—I—G—A—C—NH₂ |
|   | AP39  | C—F—G—G—R—M—D—R—I—G—A—C |
| * | AP40  | C—F—G—G—R—I—D—R—I—G—C |
| * | AP41  | C—F—G—G—R—I—D—R—I—G—C—NH₂ |
|   | AP42  | C—F—G—G—R—I—D—R—I—C |
| * | AP43  | C—F—G—G—R—M—D—R—I—C—NH₂ |
|   | AP44  | C—G—R—I—D—R—I—G—C |
| * | AP45  | C—G—R—I—D—R—I—G—C—NH₂ |
|   | AP46  | C—G—R—M—D—R—I—G—C—NH₂ |
| * | AP47  | C—R—I—D—R—I—G—A—C—NH₂ |
|   | AP48  | C—R—I—D—R—I—G—A—C |
|   | AP49  | C—R—I—D—R—I—G—C |
| * | AP50  | C—R—I—D—R—I—G—C—NH₂ |
|   | AP51  | C—R—M—D—R—I—G—C |
|   | AP52  | C—R—I—D—R—I—C |
|   | AP53  | C—R—M—D—R—I—C—NH₂ |
| * | AP54  | R—S—S—C—I—D—R—I—G—A—Q—S—G—L—G—C—N—S—F—R—Y |
| * | AP55  | R—S—S—C—F—G—R—I—D—R—I—G—A—Q—S—G—L—G—C—N—S—F—R—Y |
|   | AP56  | L—R—R—S—S—C—F—G—G—R—I—D—R—I—G—C—N—S—F—R—Y |
| * | AP57  | R—S—S—C—F—G—G—R—I—D—R—I—G—A—C—NH₂ |
| * | AP58  | R—S—S—C—F—G—G—R—I—D—R—I—G—C—NH₂ |
| * | AP59  | C—F—G—G—R—I—D—R—I—G—A—C—N—S—F—R—Y |
| * | AP60  | C—R—I—D—R—I—G—A—Q—S—G—L—G—C—N—S—F—NH₂ |
|   | AP61  | S—S—C—F—G—G—R—I—D—R—I—G—A—C—N—S—F—NH₂ |
| * | AP62  | C—F—G—R—I—D—R—I—G—A—C—N—S—F—NH₂ |
| * | AP63  | R—C—F—G—G—R—I—D—R—I—G—A—C—N—S—F—NH₂ |
| * | AP64  | C—R—I—D—R—I—G—A—Q—S—G—L—G—C—NH₂ |
| * | AP65  | C—R—I—D—R—I—G—A—Q—S—G—L—C—NH₂ |
| * | AP66  | C—F—G—G—R—I—D—R—I—G—A—Q—S—G—L—C—NH₂ |
| * | AP67  | C—F—G—G—R—I—D—R—I—G—A—Q—S—G—C—NH₂ |
| * | AP68  | C—F—G—G—R—I—D—R—I—G—A—Q—S—C—NH₂ |
| * | AP69  | C—F—G—G—R—I—D—R—I—G—A—Q—C—NH₂ |
| * | AP70  | Y—C—F—G—G—R—I—D—R—I—G—A—C—NH₂ |
| * | AP71  | C—R—I—D—R—I—G—A—Q—S—G—C—NH₂ |
| * | AP72  | C—G—G—R—M—D—R—I—G—A—C—NH₂ |
| * | AP73  | C—G—R—I—D—R—I—G—A—C—NH₂ |
| * | AP74  | C—F—G—R—I—D—R—I—G—A—C—NH₂ |
| * | AP75  | C—F—R—I—D—R—I—G—A—C—NH₂ |
| * | AP76  | R—C—F—G—G—R—I—D—R—I—G—A—C—NH₂ |
| * | AP77  | C—G—G—R—I—D—R—I—G—C—NH₂ |
| * | AP78  | C—R—I—D—R—I—G—A—Q—S—C—NH₂ |
| * | AP79  | C—F—A—G—G—R—I—D—R—I—G—A—C—NH₂ |
| * | AP80  | C—F—G—A—R—I—D—R—I—G—A—C—NH₂ |
| * | AP81  | C—F—G—G—R—I—D—R—I—Aib—A—C—NH₂ |
| * | AP82  | C—F—G—G—R—I—D—R—I—G—Aib—C—NH₂ |
| * | AP83  | [D—C]—F—G—G—R—I—D—R—I—G—A—C—NH₂ |
| * | AP84  | C—F—[D—A]—G—R—I—D—R—I—G—A—C—NH₂ |
| * | AP85  | C—F—[D—S]—G—R—I—D—R—I—G—A—C—NH₂ |
| * | AP86  | C—F—[D—L]—G—R—I—D—R—I—G—A—C—NH₂ |
| * | AP87  | C—F—G—[D—A]—R—I—D—R—I—G—A—C—NH₂ |
| * | AP88  | C—F—G—G—[D—R]—I—D—R—I—G—A—C—NH₂ |
| * | AP89  | C—F—G—G—R—[D—I]—D—R—I—G—A—C—NH₂ |
| * | AP90  | C—F—G—G—R—I—[D—D]—R—I—G—A—C—NH₂ |
| * | AP91  | C—[D—F]—G—G—R—I—D—R—I—G—A—C—NH₂ |
| * | AP92  | C—F—G—G—R—I—D—[D—R]—I—G—A—C—NH₂ |
| * | AP93  | C—F—G—G—R—I—D—R—[D—I]—G—A—C—NH₂ |
| * | AP94  | C—F—G—G—R—I—D—R—I—[D—A]—A—C—NH₂ |
| * | AP95  | C—F—G—G—R—I—D—R—I—G—[D—A]—C—NH₂ |
| * | AP96  | C—F—G—G—R—I—D—R—I—G—A—[D—C]—NH₂ |
| * | AP97  | R—S—S—C—F—[D—A]—G—R—I—D—R—I—G—A—C—NH₂ |
| * | AP98  | C—F—[D—A]—G—R—I—D—R—I—G—C—NH₂ |
| * | AP99  | Acetyl—C—F—G—G—R—I—D—R—I—G—A—C—NH₂ |
| * | AP100 | A—F—G—G—R—I—D—R—I—G—A—A—NH₂ |
| * | AP101 | A—F—G—G—R—I—D—R—I—G—A—NH₂ |
| * | AP102 | A—F—G—G—R—I—D—R—I—G—NH₂ |

|   |       |                                                      |
|---|-------|------------------------------------------------------|
| * | AP103 | A—F—G—G—R—I—D—R—I—NH₂                                |
| * | AP104 | F—G—G—R—I—D—R—I—G—A—A—NH₂                            |
| * | AP105 | G—G—R—I—D—R—I—G—A—A—NH₂                              |
| * | AP106 | G—R—I—D—R—I—G—A—A—NH₂                                |
| * | AP107 | R—I—D—R—I—G—A—A—NH₂                                  |
|   | AP108 | C—F—G—G—R—I—D—R—I—G—A—C—N—S—F—R                      |
| * | AP109 | R—C—F—G—G—R—I—D—R—I—G—A—C—N—S—F—NH₂                  |
| * | AP110 | C—F—G—G—R—I—D—R—I—G—C—N—S—F—NH₂                      |
| * | AP111 | C—F—[D—V]—G—R—I—D—R—I—G—A—C—NH₂                      |
| * | AP112 | C—F—Aib—G—R—I—D—R—I—G—A—C—NH₂                        |
| * | AP113 | C—F—G—G—R—[D—M]—D—R—I—G—A—C—NH₂                      |
| * | AP114 | C—A—G—G—R—I—D—R—I—G—A—C—NH₂                          |
|   | AP115 | C—[D—A]—G—G—R—I—D—R—I—G—A—C—NH₂                      |
|   | AP116 | C—F—G—G—R—I—D—R—[D—V]—G—A—C—NH₂                      |
|   | AP117 | C—F—G—G—R—I—E—R—I—G—A—C—NH₂                          |
|   | AP118 | A—F—G—G—R—M—D—R—I—G—NH₂                              |
| * | AP119 | F—G—G—R—I—D—R—I—NH₂                                  |
| * | AP120 | Acetyl—G—G—R—I—D—R—I—NH₂                             |
|   | AP121 | G—R—I—D—R—I—NH₂                                      |
|   | AP122 | F—G—G—R—I—D—R—I—G—NH₂                                |
|   | AP123 | G—G—R—I—D—R—I—G—NH₂                                  |
|   | AP124 | G—R—I—D—R—I—G—NH₂                                    |
|   | AP125 | R—I—D—R—I—G—NH₂                                      |
| * | AP126 | F—G—G—R—I—D—R—I—G—A—NH₂                              |
|   | AP127 | G—G—R—I—D—R—I—G—A—NH₂                                |
|   | AP128 | G—R—I—D—R—I—G—A—NH₂                                  |
|   | AP129 | R—I—D—R—I—G—A—NH₂                                    |
| * | AP130 | (desNH₂—F)—G—G—R—I—D—R—I—G—A—NH₂                     |
|   | AP131 | (desNH₂—F)—G—G—R—I—D—R—I—G—NH₂                       |
| * | AP132 | (desNH₂—F)—G—G—R—I—D—R—I—NH₂                         |
| * | AP133 | A—F—[D—A]—G—R—I—D—R—I—G—A—NH₂                        |
|   | AP134 | A—F—[D—A]—G—R—I—D—R—I—G—NH₂                          |
|   | AP135 | A—F—[D—A]—G—R—I—D—R—I—NH₂                            |
|   | AP136 | F—[D—A]—G—R—I—D—R—I—G—A—NH₂                          |
|   | AP137 | F—[D—A]—G—R—I—D—R—I—G—NH₂                            |
|   | AP138 | F—[D—A]—G—R—I—D—R—I—NH₂                              |
|   | AP139 | (desNH₂—F)—[D—A]—G—R—I—D—R—I—G—A—NH₂                 |
|   | AP140 | (desNH₂—F)—[D—A]—G—R—I—D—R—I—G—NH₂                   |
|   | AP141 | (desNH₂—F)—[D—A]—G—R—I—D—R—I—NH₂                     |
|   | AP142 | A—F—[D—S]—G—R—I—D—R—I—G—A—NH₂                        |
|   | AP143 | A—F—[D—S]—G—R—I—D—R—I—G—NH₂                          |
|   | AP144 | A—F—[D—S]—G—R—I—D—R—I—NH₂                            |
|   | AP145 | F—[D—S]—G—R—I—D—R—I—G—A—NH₂                          |
|   | AP146 | F—[D—S]—G—R—I—D—R—I—G—NH₂                            |
|   | AP147 | F—[D—S]—G—R—I—D—R—I—NH₂                              |
|   | AP148 | (desNH₂—F)—[D—S]—G—R—I—D—R—I—G—A—NH₂                 |
|   | AP149 | (desNH₂—F)—[D—S]—G—R—I—D—R—I—G—NH₂                   |
|   | AP150 | (desNH₂—F)—[D—S]—G—R—I—D—R—I—NH₂                     |
| * | AP151 | A—[D—F]—G—G—R—I—D—R—I—G—A—NH₂                        |
|   | AP152 | A—[D—F]—G—G—R—I—D—R—I—G—NH₂                          |
|   | AP153 | A—[D—F]—G—G—R—I—D—R—I—NH₂                            |
|   | AP154 | [D—F]—G—G—R—I—D—R—I—G—A—NH₂                          |
|   | AP155 | [D—F]—G—G—R—I—D—R—I—G—NH₂                            |
|   | AP156 | [D—F]—G—G—R—I—D—R—I—NH₂                              |
|   | AP157 | A—F—G—[D—A]—R—I—D—R—I—G—A—NH₂                        |
|   | AP158 | A—F—G—[D—A]—R—I—D—R—I—G—NH₂                          |
|   | AP159 | A—F—G—[D—A]—R—I—D—R—I—NH₂                            |
|   | AP160 | F—G—[D—A]—R—I—D—R—I—G—A—NH₂                          |
|   | AP161 | F—G—[D—A]—R—I—D—R—I—G—NH₂                            |
|   | AP162 | F—G—[D—A]—R—I—D—R—I—NH₂                              |
|   | AP163 | (desNH₂—F)—G—[D—A]—R—I—D—R—I—G—A—NH₂                 |
|   | AP164 | (desNH₂—F)—G—[D—A]—R—I—D—R—I—G—NH₂                   |
|   | AP165 | (desNH₂—F)—G—[D—A]—R—I—D—R—I—NH₂                     |
|   | AP166 | A—F—G—G—R—I—D—R—I—G—[D—A]—NH₂                        |
|   | AP167 | F—G—G—R—I—D—R—I—G—[D—A]—NH₂                          |
|   | AP168 | (desNH₂—F)—G—G—R—I—D—R—I—G—[D—A]—NH₂                 |
|   | AP169 | A—F—G—G—R—I—D—R—I—[D—A]—A—NH₂                        |
|   | AP170 | F—G—G—R—I—D—R—I—[D—A]—A—NH₂                          |
|   | AP171 | (desNH₂—F)—G—G—R—I—D—R—I—[D—A]—A—NH₂                 |
|   | AP172 | A—F—G—G—R—I—D—R—I—[D—A]—NH₂                          |
|   | AP173 | F—G—G—R—I—D—R—I—[D—A]—NH₂                            |
|   | AP174 | (desNH₂—F)—G—G—R—I—D—R—I—[D—A]—NH₂                   |
|   | AP175 | Y—A—F—G—G—R—I—D—R—I—G—A—NH₂                          |
|   | AP176 | A—F—G—G—R—I—D—R—I—G—Y—NH₂                            |
|   | AP177 | A—F—G—G—R—I—E—R—I—G—A—NH₂                            |
|   | AP178 | A—F—G—G—K—I—E—R—I—G—A—NH₂                            |
|   | AP179 | A—F—G—G—K—I—D—R—I—G—A—NH₂                            |
|   | AP180 | A—F—G—G—R—I—D—K—I—G—A—NH₂                            |
|   | AP181 | (desNH₂—F)—G—G—R—M—D—R—I—G—A—NH₂                     |
|   | AP182 | (desNH₂—F)—G—G—R—M—D—R—I—G—NH₂                       |
|   | AP183 | (desNH₂—F)—G—G—R—M—D—R—I—NH₂                         |
|   | AP184 | A—F—[D—A]—G—R—M—D—R—I—G—A—NH₂                        |

-continued

| | |
|---|---|
| AP185 | A—F—[D—A]—G—R—M—D—R—I—G—NH₂ |
| AP186 | A—F—[D—A]—G—R—M—D—R—I—NH₂ |
| AP187 | F—[D—A]—G—R—M—D—R—I—G—A—NH₂ |
| AP188 | F—[D—A]—G—R—M—D—R—I—G—NH₂ |
| AP189 | F—[D—A]—G—R—M—D—R—I—NH₂ |
| AP190 | (desNH₂—F)—[D—A]—G—R—M—D—R—I—G—A—NH₂ |
| AP191 | (desNH₂—F)—[D—A]—G—R—M—D—R—I—G—NH₂ |
| AP192 | (desNH—F)—[D—A]—G—R—M—D—R—I—NH₂ |
| AP193 | A—F—[D—S]—G—R—M—D—R—I—G—A—NH₂ |
| AP194 | A—F—[D—S]—G—R—M—D—R—I—G—NH₂ |
| AP195 | A—F—[D—S]—G—R—M—D—R—I—NH₂ |
| AP196 | F—[D—S]—G—R—M—D—R—I—G—A—NH₂ |
| AP197 | F—[D—S]—G—R—M—D—R—I—G—NH₂ |
| AP198 | F—[D—S]—G—R—M—D—R—I—NH₂ |
| AP199 | (desNH₂—F)—[D—S]—G—R—M—D—R—I—G—A—NH₂ |
| AP200 | (desNH₂—F)—[D—S]—G—R—M—D—R—I—G—NH₂ |
| AP201 | (desNH₂—F)—[D—S]—G—R—M—D—R—I—NH₂ |
| AP202 | A—[D—F]—G—G—R—M—D—R—I—G—A—NH₂ |
| AP203 | A—[D—F]—G—G—R—M—D—R—I—G—NH₂ |
| AP204 | A—[D—F]—G—G—R—M—D—R—I—NH₂ |
| AP205 | [D—F]—G—G—R—M—D—R—I—G—A—NH₂ |
| AP206 | [D—F]—G—G—R—M—D—R—I—G—NH₂ |
| AP207 | [D—F]—G—G—R—M—D—R—I—NH₂ |
| AP208 | A—F—G—[D—A]—R—M—D—R—I—G—A—NH₂ |
| AP209 | A—F—G—[D—A]—R—M—D—R—I—G—NH₂ |
| AP210 | A—F—G—[D—A]—R—M—D—R—I—NH₂ |
| AP211 | F—G—[D—A]—R—M—D—R—I—G—A—NH₂ |
| AP212 | F—G—[D—A]—R—M—D—R—I—G—NH₂ |
| AP213 | F—G—[D—A]—R—M—D—R—I—NH₂ |
| AP214 | (desNH₂—F)—G—[D—A]—R—M—D—R—I—G—A—NH₂ |
| AP215 | (desNH₂—F)—G—[D—A]—R—M—D—R—I—G—NH₂ |
| AP216 | (desNH₂—F)—G—[D—A]—R—M—D—R—I—NH₂ |
| AP217 | A—F—G—G—R—M—D—R—I—G—[D—A]—NH₂ |
| AP218 | F—G—G—R—M—D—R—I—G—[D—A]—NH₂ |
| AP219 | (desNH₂—F)—G—G—R—M—D—R—I—G—[D—A]—NH₂ |
| AP220 | A—F—G—G—R—M—D—R—I—[D—A]—A—NH₂ |
| AP221 | F—G—G—R—M—D—R—I—[D—A]—A—NH₂ |
| AP222 | (desNH₂—F)—G—G—R—M—D—R—I—[D—A]—A—NH₂ |
| AP223 | A—F—G—G—R—M—D—R—I—[D—A]—NH₂ |
| AP224 | F—G—G—R—M—D—R—I—[D—A]—NH₂ |
| AP225 | (desNH₂—F)—G—G—R—M—D—R—I—[D—A]—NH₂ |
| AP226 | Y—A—F—G—G—R—M—D—R—I—G—A—NH₂ |
| AP227 | A—F—G—G—R—M—D—R—I—G—Y—NH₂ |
| AP228 | A—F—G—G—R—M—E—R—I—G—A—NH₂ |
| AP229 | A—F—G—G—K—M—E—R—I—G—A—NH₂ |
| AP230 | A—F—G—G—K—M—D—R—I—G—A—NH₂ |
| AP231 | A—F—G—G—R—M—D—K—I—G—A—NH₂ |
| AP232 | R—S—S—C—F—G—G—R—M—D—R—I—G—A—C—NH₂ |
| AP233 | R—S—S—C—F—G—G—R—M—D—R—I—G—C—NH₂ |
| AP234 | C—F—G—G—R—M—D—R—I—G—A—C—N—S—F—R—Y |
| AP235 | C—R—M—D—R—I—G—A—Q—S—G—L—G—C—N—S—F—NH₂ |
| AP236 | S—S—C—F—G—G—R—M—D—R—I—G—A—C—N—S—F—NH₂ |
| AP237 | C—F—G—G—R—M—D—R—I—G—A—C—N—S—F—NH₂ |
| AP238 | R—C—F—G—G—R—M—D—R—I—G—A—C—N—S—F—NH₂ |
| AP239 | C—R—M—D—R—I—G—A—Q—S—G—L—G—C—NH₂ |
| AP240 | C—R—M—D—R—I—G—A—Q—S—G—L—C—NH₂ |
| AP241 | C—F—G—G—R—M—D—R—I—G—A—Q—S—G—L—C—NH₂ |
| AP242 | C—F—G—G—R—M—D—R—I—G—A—Q—S—G—C—NH₂ |
| AP243 | C—F—G—G—R—M—D—R—I—G—A—Q—S—C—NH₂ |
| AP244 | C—F—G—G—R—M—D—R—I—G—A—Q—C—NH₂ |
| AP245 | Y—C—F—G—G—R—M—D—R—I—G—A—C—NH₂ |
| AP246 | C—R—M—D—R—I—G—A—Q—S—G—C—NH₂ |
| AP247 | C—G—R—M—D—R—I—G—A—C—NH₂ |
| *AP248 | C—F—G—R—M—D—R—I—G—A—C—NH₂ |
| AP249 | C—F—R—M—D—R—I—G—A—C—NH₂ |
| AP250 | R—C—F—G—G—R—M—D—R—I—G—A—C—NH₂ |
| AP251 | C—G—G—R—M—D—R—I—G—C—NH₂ |
| AP252 | C—R—M—D—R—I—G—A—Q—S—C—NH₂ |
| AP253 | C—F—A—G—R—M—D—R—I—G—A—C—NH₂ |
| AP254 | C—F—G—A—R—M—D—R—I—G—A—C—NH₂ |
| AP255 | C—F—G—G—R—M—D—R—I—Aib—A—C—NH₂ |
| AP256 | C—F—G—G—R—M—D—R—I—G—Aib—C—NH₂ |
| AP257 | [D—C]—F—G—G—R—M—D—R—I—G—A—C—NH₂ |
| AP258 | C—F—[D—A]—G—R—M—D—R—I—G—A—C—NH₂ |
| AP259 | C—F—[D—S]—G—R—M—D—R—I—G—A—C—NH₂ |
| AP260 | C—F—[D—L]—G—R—M—D—R—I—G—A—C—NH₂ |
| AP261 | C—F—G—[D—A]—R—M—D—R—I—G—A—C—NH₂ |
| AP262 | C—F—G—G—[D—R]—M—D—R—I—G—A—C—NH₂ |
| AP263 | C—F—G—G—R—[D—M]—D—R—I—G—A—C—NH₂ |
| AP264 | C—F—G—G—R—M—[D—D]—R—I—G—A—C—NH₂ |
| AP265 | C—[D—F]—G—G—R—M—D—R—I—G—A—C—NH₂ |
| AP266 | C—F—G—G—R—M—D—[D—R]—I—G—A—C—NH₂ |

| | |
|---|---|
| AP267 | C—F—G—G—R—M—D—R—[D—I]—G—A—C—NH₂ |
| AP268 | C—F—G—G—R—M—D—R—I—[D—A]—A—C—NH₂ |
| AP269 | C—F—G—G—R—M—D—R—I—G—[D—A]—C—NH₂ |
| AP270 | C—F—G—G—R—M—D—R—I—G—A—[D—C]—NH₂ |
| AP271 | R—S—S—C—F—[D—A]—G—R—M—D—R—I—G—A—C—NH₂ |
| AP272 | C—F—[D—A]—G—R—M—D—R—I—G—C—NH₂ |
| AP273 | Acetyl—C—F—G—G—R—M—D—R—I—G—A—C—NH₂ |
| AP274 | A—F—G—G—R—M—D—R—I—G—A—A—NH₂ |
| AP275 | A—F—G—G—R—M—D—R—I—G—A—NH₂ |
| AP276 | A—F—G—G—R—M—D—R—I—NH₂ |
| AP277 | F—G—G—R—M—D—R—I—G—A—A—NH₂ |
| AP278 | G—G—R—M—D—R—I—G—A—A—NH₂ |
| AP279 | G—R—M—D—R—I—G—A—A—NH₂ |
| AP280 | R—M—D—R—I—G—A—A—NH₂ |
| AP281 | C—F—G—G—R—M—D—R—I—G—A—C—N—S—F—NH₂ |
| AP282 | R—C—F—G—G—R—M—D—R—I—G—A—C—N—S—F—NH₂ |
| AP283 | C—F—G—G—R—M—D—R—I—G—C—N—S—F—NH₂ |
| AP284 | C—F—[D—V]—G—R—M—D—R—I—G—A—C—NH₂ |
| AP285 | C—F—Aib—G—R—M—D—R—I—G—A—C—NH₂ |
| AP286 | C—A—G—G—R—M—D—R—I—G—A—C—NH₂ |
| AP287 | C—[D—A]—G—G—R—M—D—R—I—G—A—C—NH₂ |
| AP288 | C—F—G—G—R—M—D—R—[D—V]—G—A—C—NH₂ |
| AP289 | C—F—G—G—R—M—E—R—I—G—A—C—NH₂ |
| AP290 | F—G—G—R—M—D—R—I—NH₂ |
| AP291 | Acetyl—G—G—R—M—D—R—I—NH₂ |
| AP292 | G—R—M—D—R—I—NH₂ |
| AP293 | F—G—G—R—M—D—R—I—G—NH₂ |
| AP294 | G—G—R—M—D—R—I—G—NH₂ |
| AP295 | G—R—M—D—R—I—G—NH₂ |
| AP296 | R—M—D—R—I—G—NH₂ |
| AP297 | F—G—G—R—M—D—R—I—G—A—NH₂ |
| AP298 | G—G—R—M—D—R—I—G—A—NH₂ |
| AP299 | G—R—M—D—R—I—G—A—NH₂ |
| AP300 | R—M—D—R—I—G—A—NH₂ |

In each of the above examples, designated "*", amino acid analysis demonstrated that the appropriate amino acid sequence of the peptide was obtained.

II. Biological Testing

Biological activity data for selected analog peptides which were synthesized as disclosed above is presented below as biochemical, isolated tissue and whole mammal bioassays.

1. Receptor binding assays

Specific ANP receptors sites have been identified on target tissues, such as kidney, adrenal, blood vessels, and cultured cells. Napier, M. A., et al., Proc. Nat. Acad. Sci. U.S.A. 81:5946–5940 (1984); DeLean, A., et al., Endocrinology 115:1636–1638 (1984); Schenk, D. B., et al., Biochem. Biophys. Res. Comm. 127:433–442 (1985). Since the binding of ANP or ANP analogs to these specific receptor sites is a prerequisite of biological activity, assays examining binding of ANP analogs to these receptors is predictive of biological activity.

An assay has been developed, generally in accordance with the disclosure of Schenk, supra, which evaluates the ability of ANP analogs to compete with an iodinated native Atrial Natriuretic Peptide (identified as [$^{125}$I]-rANP(126-150) and having the amino acid sequence R—S—S—C—F—G—G—R—I—D—R—I—G—A—Q—S—G—L—G—C—N—S—F—R—Y—OH) for binding to cultured bovine aortic smooth muscle (BASM) cells and bovine endothelial (BAE) cells. Analogous "competitive displacement" receptor binding assays are considered commonplace in the art for examining specific ligand-receptor interactions. An example of the results of this ANP-receptor binding assay is presented in FIG. 1.

In this assay, 0.5 nM [$^{125}$I]-rANP(126-150) was incubated in each individual well of BASM in the presence of varying amounts of unlabeled rANP(126-150) or a compound of the present invention having the amino acid sequence:

AP25
R—S—S—C—R—I—D—R—I-
—G—A—Q—S—G—L—G—C—N—S—F—
R—Y

AP37
C—F—G—G—R—I—D—R—I-
—G—A—C—NH₂

AP101
A—F—G—G—R—I—D—R—I—G—A—NH₂
or

AP132
(desNH₂—F)—G—G—R—I—D—R—I—NH₂

As shown in FIG. 1 increasing concentrations of rANP(126-150), or analog peptides AP25, AP37, AP101 or AP132 (a linear eight amino acid peptide analog), effectively prevent [$^{125}$I]-rANP(126-150) binding to BASM-associated receptors. The concentration of unlabeled peptide at which 50% of maximal [$^{125}$I]-rANP(126-150) binding is displaced is called Ki(app) and reflects receptor-binding affinity. Therefore, hypothetical peptide A, with a Ki(app)=100 nM, displays substantially weaker interaction with a receptor than hypothetical peptide B with a Ki(app)=10 nM. Assuming these ANP analogs are agonists at one or more ANP receptor sites, then increased receptor affinity should reflect increased biological potency.

Table IA, IB, IC, ID and IE present data which compare the concentrations at which analog compounds of the present invention displace [$^{125}$I]-rANP(126-150) binding from specific receptor sites on BASM or BAE.

TABLE IA

| Peptide | Sequence | Ki(app)(nM) |
|---|---|---|
| rANP(126-150) | R—S—S—C—F—G—G—R—I—D—R—I—G—A—Q—S—G—L—G—C—N—S—F—R—Y | 7.26 |
| AP23 | R—S—S—C—G—G—R—I—D—R—I—G—A—Q—S—G—L—G—C—N—S—F—R—Y | 7.76 |
| AP24 | R—S—S—C—G—R—I—D—R—I—G—A—Q—S—G—L—G—C—N—S—F—R—Y | 25.2 |
| AP25 | R—S—S—C—R—I—D—R—I—G—A—Q—S—G—L—G—C—N—S—F—R—Y | 8.62 |
| AP54 | R—S—S—C—I—D—R—I—G—A—Q—S—G—L—G—C—N—S—F—R—Y | >>40 |

Table IA compares receptor binding affinity (Ki-(app)) of rANP(126-150) with Ki(app) of analog peptides wherein $X_1$ is R—S—S, $X_3$ is A—Q—S—G—L—G, $X_4$ is N—S—F—R—Y, $X_2$ has been selected from the group consisting of G—G, G and desX$_2$, and wherein $AA_8$ has been selected from the group consisting of R and desAA$_8$.

Although analog peptide AP24, where $X_2$ is G, has a weaker apparent affinity, analog peptide AP23, where $X_2$ is G—G and analog peptide AP25, where $X_2$ is desX$_2$, exhibit equivalent receptor affinities to that of rANP(126-150). However, receptor binding capacity is substantially diminished for AP54. Thus AP54 should exhibit weaker biological activity.

TABLE IB

| Peptide | Sequence | Ki(app)(nM) |
|---|---|---|
| rANP(126-150) | R—S—S—C—F—G—G—R—I—D—R—I—G—A—Q—S—G—L—G—C—N—S—F—R—Y | 7.26 |
| AP1 | R—S—S—C—F—G—G—R—I—D—R—I—G—A—Q—S—G—C—N—S—F—R—Y | 6.88 |
| AP3 | R—S—S—C—F—G—G—R—I—D—R—I—G—A—Q—S—C—N—S—F—R—Y | 9.12 |
| AP4 | R—S—S—C—F—G—G—R—I—D—R—I—G—A—A—C—N—S—F—NH$_2$ | 1.41 |
| AP17 | R—S—S—C—F—G—G—R—I—D—R—I—G—A—Q—C—N—S—F—R—Y | 7.35 |
| AP20 | R—S—S—C—F—G—G—R—I—D—R—I—G—A—C—N—S—F—R—Y | 7.50 |
| AP21 | R—S—S—C—F—G—G—R—I—D—R—I—G—C—N—S—F—R—Y | 15.15 |
| AP22 | R—S—S—C—F—G—G—R—I—D—R—I—C—N—S—F—R—Y | >40 |

Table IB presents data which compares the Ki(app) of rANP(126-150) with analog peptides wherein $X_1$ is R—S—S, $X_2$ is F—G—G, $X_4$ is N—S—F—R—Y or N—S—F—NH$_2$, $X_3$ is selected from the group consisting of A—Q—S—G, A—Q—S, A—Q, A and desX$_3$, and wherein $AA_{13}$ has been selected from the group consisting of G and desAA$_{13}$. A significant decline in the receptor-binding affinity was not observed in any peptide analog except analog peptide AP22, where $X_3$ is desX$_3$ and $AA_{13}$ is desAA$_{13}$.

TABLE IC

| Peptide | Sequence | Ki(app)(nM) |
|---|---|---|
| rANP(126-150) | R—S—S—C—F—G—G—R—I—D—R—I—G—A—Q—S—G—L—G—C—N—S—F—R—Y | 7.26 |
| AP20 | R—S—S—C—F—G—G—R—I—D—R—I—G—A—C—N—S—F—R—Y | 7.50 |
| AP36 | C—F—G—G—R—I—D—R—I—G—A—C | 14.92 |
| AP37 | C—F—G—G—R—I—D—R—I—G—A—C—NH$_2$ | 13.40 |
| AP62 | C—F—G—G—R—I—D—R—I—G—A—C—N—S—F—NH$_2$ | 5.96 |
| AP109 | R—C—F—G—G—R—I—D—R—I—G—A—C—N—S—F—NH$_2$ | 4.97 |
| AP110 | C—F—G—G—R—I—D—R—I—G—C—N—S—F—NH$_2$ | 6.51 |
| AP64 | C—R—I—D—R—I—G—A—Q—S—G—L—G—C—NH$_2$ | 12.39 |
| AP67 | C—F—G—G—R—I—D—R—I—G—A—Q—S—G—C—NH$_2$ | 7.08 |
| AP69 | C—F—G—G—R—I—D—R—I—G—A—Q—C—NH$_2$ | 2.45 |
| AP65 | C—R—I—D—R—I—G—A—Q—S—G—L—C—NH$_2$ | 14.04 |
| AP70 | Y—C—F—G—G—R—I—D—R—I—G—A—C—NH$_2$ | 7.07 |
| AP83 | [D—C]—F—G—G—R—I—D—R—I—G—A—C—NH$_2$ | 5.75 |
| AP91 | C—[D—F]—G—G—R—I—D—R—I—G—A—C—NH$_2$ | 24.03 |
| AP84 | C—F—[D—A]—G—R—I—D—R—I—G—A—C—NH$_2$ | 13.29 |
| AP85 | C—F—[D—S]—G—R—I—D—R—I—G—A— | 5.25 |

TABLE IC-continued

| Peptide | Sequence | Ki(app)(nM) |
|---|---|---|
| | C—NH₂ | |
| AP86 | C—F—[D—L]—G—R—I—D—R—I—G—A—C—NH₂ | 14.04 |
| AP111 | C—F—[D—V]—G—R—I—D—R—I—G—A—C—NH₂ | 10.68 |
| AP112 | C—F—Aib—G—R—I—D—R—I—G—A—C—NH₂ | 69.57 |
| AP82 | C—F—G—G—R—I—D—R—I—G—Aib—C—NH₂ | 4.43 |
| AP113 | C—F—G—G—R—[D—M]—D—R—I—G—A—C—NH₂ | 15.77 |
| AP89 | C—F—G—G—R—[D—I]—D—R—I—G—A—C—NH₂ | >100 |
| AP90 | C—F—G—G—R—I—[D—D]—R—I—G—A—C—NH₂ | >100 |
| AP92 | C—F—G—G—R—I—D—[D—R]—I—G—A—C—NH₂ | >100 |
| AP94 | C—F—G—G—R—I—D—R—I—[D—A]—A—C—NH₂ | 26.73 |
| AP95 | C—F—G—G—R—I—D—R—I—G—A—[D—A]—C—NH₂ | 20.34 |
| AP96 | C—F—G—G—R—I—D—R—I—G—A—[D—C]—NH₂ | 3.75 |
| AP114 | C—A—G—G—R—I—D—R—I—G—A—C—NH₂ | >100 |
| AP115 | C—[D—A]—G—G—R—I—D—R—I—G—A—C—NH₂ | 18.27 |

Table IC presents data which compares Ki(app)'s of analog peptides wherein $X_1$ is selected from the group consisting of R—S—S, R and desX₁; $X_2$ is selected from the group consisting of F—G—G, A—G—G, [D—A]—G—G, F—[D—A]—G, F—[D—S]—G, F—[D—L]—G, F—[D—V]—G and desX₂; $X_3$ is selected from the group consisting of A, Aib, A—Q, A—Q—S—G and desX₃; and $X_4$ is selected from the group consisting of N—S—F—R—Y, N—S—F—NH₂, NH₂ and desX₄. No significant decline in the receptor-binding affinity was observed for many analog peptides of this series. This demonstrates a family of peptides that interact with at least one ANP-specific receptor on BASM. This binding reflects the ability of the ANP analogs to elicit biological responses.

The short 12 amino acid peptides where $X_3$ is A (represented as COOH-terminal carboxylic acids) for example, analog peptide AP36 or (amides) analog peptide AP37 generally exhibit comparable receptor binding affinity to rANP(126-150) or analog peptide AP20. D-amino acid substitutions increase affinity in some instances and markedly decrease affinity in other cases. This basic observation demonstrates that, although Amino- or Carboxy-terminal extensions on the disulfide-bridged ring (with $X_3$ present as A) may have some effects on bioreactivity, they are not required for receptor binding. Furthermore, alterations in bioresponsiveness with various Amino- or Carboxy-terminal extensions (where $X_1$ and/or $X_4$ can each have selected amino acid sequences) can be discerned from the results presented herein. Thus, analog peptides AP36 and AP37, which exhibit substantial ANP-receptor affinity, will be active with any of the disclosed Amino-terminal extensions (wherein $X_1$ is selected from the group consisting of S—L—R—R—S—S, L—R—R—S—S, R—R—S—S, R—S—S, and S) or Carboxy-terminal extensions (wherein $X_4$ is selected from the group consisting of N—S—F—R—Y, N—S—F—R, N—S—F, N—S and N) and the present invention provides analogs which include all of these possibilities, or combinations thereof.

TABLE ID

| Peptide | Sequence | Ki(app) |
|---|---|---|
| rANP(126-150) | R—S—S—C—F—G—G—R—I—D—R—I—G—A—S—Q—G—L—G—C—N—S—F—R—Y | 7.50 |
| AP104 | F—G—G—R—I—D—R—I—G—A—A—NH₂ | 2.50 |
| AP101 | A—F—G—G—R—I—D—R—I—G—A—NH₂ | 6.51 |
| AP102 | A—F—G—G—R—I—D—R—I—G—NH₂ | 3.00 |
| AP103 | A—F—G—G—R—I—D—R—I—NH₂ | 2.50 |
| AP132 | (desNH₂—F)—G—G—R—I—D—R—I—NH₂ | 19.50 |
| AP125 | R—I—D—R—I—G—NH₂ | >100 |
| AP105 | G—G—R—I—D—R—I—G—A—A—NH₂ | >100 |

Table ID represents peptides where $X_1$ is desX₁, $X_2$ is selected from the group consisting of (desNH₂—F—)—G—G, F—G—G, G—G, and desX₂, $X_3$ is A or desX₃, AA₁₃ is G or desAA₁₃, AA₄ is A or desAA₄, AA₂₀ is A or desAA₂₀ and $X_4$ is desX₄. These peptide analogs are no longer cyclized (e.g., disulfide bridged). However, they retain receptor binding activity to BASM and peptides AP101, AP102, AP103 and AP104 appear to exhibit increased receptor affinity. Furthermore, the linear eight amino acid peptide AP132 also binds avidly to specific ANP receptors on BASM. Only AP125 (desX₂) and AP105 (where $X_2$ is G—G) have diminished receptor affinity in this bioassay. Thus, one expects that peptides that bind to BASM will exhibit biological activity. Although the spectrum and magnitude of biological responses may differ from those of rANP(126-150), the peptides are nevertheless biologically active and predictably have therapeutic value.

TABLE IE

| Peptide | Ki(app) |
|---|---|
| rANP(126-150) | 7.50 |
| angiotensin II | >>100 |
| glucagon | >>100 |
| parathyroid hormone | >>100 |
| γ-MSH | >>100 |

Table IE provides data which compares ANP-receptor interactions of rANp(126-150) with those of unrelated peptide hormones angiotensin II, glucagon, parathyroid hormone and γ-MSH. As shown, only rANP(126-150) displays detectable ANP-receptor affinity. This attests to the relevant ANP-specificity of this receptor.

2. Diuresis in anesthetized rats

The biological activity of analog compounds of the present invention can also be demonstrated in anesthetized rats. In one set of examples, cannulae were placed in the left and right ureters and femoral vein of anesthetized rats and urine was collected from the ureters. Analog peptides were administered via the femoral vein. Saline was infused for one hour and urine was then collected for 6 additional five minute collection periods and urine volume was determined gravimetrically.

Following these 6 baseline collection periods, various analog peptides were infused for 30 minutes and urine volume was measured in five minute periods during infusion and for 60 minutes following infusion (at which time rats were returned to saline). Data was examined by averaging urine flow rates for six five-minute baseline control periods immediately preceding infusion, and comparing values during and after administration of peptides with the "baseline" control values. Responses to peptides are thus evaluated and plotted as the percent of baseline control responses. Specific examples are shown in FIGS. 2A-F. The error bars at the beginning of the graphs represent baseline values ± standard deviations. Responses to peptides that are significantly above baseline ± SD can thus be interpreted as being statistically significant increases.

As shown in FIG. 2A-F, diuretic responses correlate with predictions from receptor binding studies. Analog peptides AP20, AP21, AP25, AP37 and AP101, all of which contain shortened amino acid sequences for $X_2$ or $X_3$, significantly increased urine flow rate (urine volume) when infused at 5 µg/min, 5 µg/min, 5 µg/min, 10 µg/min and 5 µg/min, respectively. Thus, these analog peptides, including the 12 amino acid peptide C—F—G—G—R—I—D—R—I—G—A—C—NH₂ (disulfide bridge not shown), and 11 amino acid peptide A—F—G—G—R—I—D—R—I—G—A—NH₂ all induce diuresis.

Therefore, these examples disclose a core sequence which appears to be required for this biological response. One Atrial Natriuretic Peptide tested for comparison, AP54, exhibited far weaker binding affinities than the analog peptides of the present invention (see Table IA) and was inactive at doses examined in this assay. Thus, the receptor binding analysis (Tables IA-E) appears to predict diuretic potency.

3. Blood prressure responses in anesthetized rats

Compounds of the present invention also lowered blood pressure when administered as a bolus or infusion to anesthetized rats. Table II presents data which compares the blood pressure effects of representative compounds of the present invention, including analog peptide AP20 (R—S—S—C—F—G—G—R—I—D—R—I—G—A—C—N—S—F—R—Y) and analog peptide AP37 (C—F—G—G—R—I—D—R—I—G—A—C—NH₂), with that of rANP(126-150), following administration by infusion.

TABLE II

| Peptide | Structure | Dose (p mol/kg/min) | Δ Blood Pressure |
|---|---|---|---|
| rANP (126-150) | R—S—S—C—F—G—G—R—I—D—R—I—G—A—Q—S—G—L—G—C—N—S—F—R—Y | 183 | −39 ± 5 |
| AP20 | R—S—S—C—F—G—G—R—I—D—R—I—G—A—C—N—S—F—R—Y | 733 | −34 ± 3 |
| AP37 | C—F—G—G—R—I—D—R—I—G—A—C—NH₂ | 7330 | −14 ± 3 |

As shown, each of the analog peptides lowered blood pressure significantly. While analog peptide AP37 exhibited a weaker effect on blood pressure at a substantially higher dose (40× that of rANP(126-150)) it nevertheless was hypotensive. It has also been found that analog peptides AP40 and AP41 exhibit activity similar to AP37.

It has been demonstrated that analog peptide compounds of the present invention wherein $X_1$ is Amino and $X_4$ is Carboxy or Amido display the desired biological activity when compared to rANP(126-150). Furthermore, it has been further shown that biological activity is displayed by compounds produced in accordance with the present invention wherein $X_2$ is des$X_2$ and in compounds wherein $X_3$ is des$X_3$. These regions are therefore shown not to be required for the desired activity displayed by the present compounds. Thus, the administration to mammalian hosts of therapeutically effective amounts of the additional disclosed analog peptides, or pharmaceutical compositions containing these analog peptides, can be used to substantially increase natriuresis and diuresis and/or alter the vascular caliber. Furthermore, administration of selected analog peptides within the scope of the present invention can be used to treat cases of hypertension or various edematous states whose etiology does not require the full range of biological activity provided by native ANP compounds.

D. Natriuresis and diuresis in the isolated perfused rat kidney

The biological actions of the ANP analogs can also be demonstrated in the isolated perfused rat kidney, as described in Camarjo, M. J. F. et al.. Am. J. Physiol., 246: F447-F456 (1984). In a particular set of examples, the effect of the 15 amino acid peptide R—S—S—C—F—G—G—R—I—D—R—I—G—A—C—NH₂ (peptide AP57) at a concentration of $10^{-7}$M, was demonstrated in the intact kidney. The results were as presented in Table III.

TABLE III

EFFECT OF AP57 ON DOSE-RESPONSE CURVES OF rANP(123-150) IN THE ISOLATED PERFUSED RAT KIDNEY

| | GFR (ml/min) | FF (%) | RVR (mmHg/ml/min) | $U_{Na}V$ (µEq/min) | $FE_{Na}$ (%) | V (µl/min) |
|---|---|---|---|---|---|---|
| A. CONTROL KIDNEYS (N = 5) | | | | | | |
| | 0.48 ± 0.06 | 1.21 ± 0.15 | 2.30 ± 0.12 | 0.37 ± 0.08 | 0.56 ± 0.09 | 16.5 ± 2.0 |
| B. AP57 ($10^{-7}$ M) (N = 4) | | | | | | |
| | 0.55 ± 0.07 | 1.37 ± 0.22 | 2.27 ± 0.17 | 0.17 ± 0.04 | 0.24 ± 0.08 | 13.8 ± 2.0 |
| C. rANP(123-150) ($10^{-11}$ TO $10^{-8}$ M) (N = 4) | | | | | | |
| [C] | 0.45 ± 0.06 | 1.22 ± 0.20 | 2.29 ± 0.15 | 0.30 ± 0.05 | 0.50 ± 0.10 | 15.0 ± 1.8 |
| $10^{-11}$ | 0.53 ± 0.04 | 1.33 ± 0.20 | 2.36 ± 0.20 | 0.53 ± 0.14 | 0.72 ± 0.19 | 21.8 ± 1.7 |
| $10^{-10}$ | 0.66 ± 0.07 | 1.76 ± 0.19 | 2.51 ± 0.26 | 1.13 ± 0.43 | 1.21 ± 0.44 | 35.5 ± 5.7 |
| $10^{-9}$ | 0.82 ± 0.07 | 2.30 ± 0.41 | 2.64 ± 0.35 | 3.22 ± 0.92 | 2.78 ± 0.89 | 74.0 ± 14.8 |
| $10^{-8}$ | 0.80 ± 0.08 | 2.23 ± 0.44 | 2.66 ± 0.32 | 4.78 ± 1.15 | 4.12 ± 0.94 | 96.6 ± 24.0 |
| D. rANP(123-150) ($10^{-11}$ to $10^{-8}$ M) IN PRESENCE OF AP57 ($10^{-7}$ M)$^3$ (N = 4) | | | | | | |
| [C] | 0.65 ± 0.06 | 1.57 ± 0.27 | 2.21 ± 0.21 | 0.17 ± 0.05 | 0.18 ± 0.04 | 16.3 ± 2.0 |
| $10^{-11}$ | 0.80 ± 0.08 | 2.04 ± 0.15 | 2.50 ± 0.15 | 0.45 ± 0.10 | 0.41 ± 0.11 | 31.0 ± 3.7 |
| $10^{-10}$ | 0.93 ± 0.04 | 2.65 ± 0.20 | 2.80 ± 0.31 | 1.76 ± 0.25 | 1.33 ± 0.20 | 70.6 ± 4.2 |
| $10^{-9}$ | 0.99 ± 0.07 | 2.81 ± 0.40 | 2.79 ± 0.34 | 6.03 ± 1.37 | 4.08 ± 0.72 | 139 ± 14 |
| $10^{-8}$ | 0.84 ± 0.13 | 2.30 ± 0.47 | 2.63 ± 0.33 | 6.47 ± 2.29 | 4.77 ± 1.22 | 132 ± 33 |

GFR = glomerular filtration rate; FF = filtration fraction; RVR = renal vascular resistance; $U_{Na}V$ = uninary sodium excretion rate; $FE_{na}$ = fractional sodium excretion; V = urine flow rate. Results are presentedas mean ' SE, with the number of kidneys presented for each test phase. In the phase demonstrating the effect of AP57 on the dose response curve of rANP(123-150), $10^{-7}$ M AP57 was added 30 minutes before the addition of increasing doses of rANP(123-150).

Despite having natriuretic and diuretic activities in an intact rat, analog peptide AP57 was not active in the isolated perfused rat kidney at a concentration of $10^{-7}$M (Table III - Compare III.B to III.A).

Peptide AP57 was then tested for its ability to modulate the renal responses to the peptide
S—L—R—R—S—S—C—F—G—G—R—I-
—D—R—I-
—G—A—Q—S—G—L—G—C—N—S—F—R—Y,
designated rANP(123-150). As shown in Table III, rANP(123-150) increases glomerular filtration rate, renal vascular resistance, filtration fraction, urinary sodium excretion rate, fractional excretion of sodium and urinary flow rate in a dose dependent manner in the concentration range from $10^{-11}$ to $10^{-7}$M. Also shown in Table III, pretreatment of the isolated kidney with $10^{-7}$M AP57 causes the subsequent responses to rANP(123-150) to occur at substantially reduced concentrations. Analog peptide AP57, despite being apparently inactive in this in vitro model, increased the potency of rANP(123-150) approximately 10-fold. Thus, AP57 potentiates the activity of rANP(123-150).

Table IV shows that both rANP(123-150) and AP57 complete for specific [$^{125}$I]-rANP(123-150) binding to the cortex of the kidney.

TABLE IV

| RATIO OF BOUND/FREE [$^{125}$I]—rANP(123-150) | | |
|---|---|---|
| | WHOLE KIDNEY | OUTER CORTEX |
| [$^{125}$I]—rANP (123-150) (4 × $10^{-12}$ M) (N = 3) | 122 ± 46 | 176 ± 23 |
| [$^{125}$I]—rANP (123-150) (4 × $10^{-12}$ M) + rANp(123-150) ($10^{-7}$ M) (N = 3) | 0.63 ± 0.27 | 0.77 ± 0.30 |
| [$^{125}$I]—rANP (123-150) (4 × $10^{-12}$ M) + AP57 ($10^{-7}$ M) (N = 3) | 1.27 ± 0.32 | 1.68 ± 0.44 |

These cortical-associated receptor sites may be involved in the clearance and removal of the Atrial Natriuretic Peptides. Thus, AP57 may block the clearance of rANP(123-150) in the isolated kidney model, thereby explaining its ability to potentiate the effects of rANP(123-150). Furthermore, if AP57 blocks clearance of endogenous ANP's, it may explain the natriuretic, diuretic and vasorelaxant responses to this peptides in vitro. Thus, AP57 and related analog peptides, which contain variable internal deletions in the peptide sequence of the native ANP's, may modulate the activity of endogenous ANP's, possibly by altering clearance. However, despite the mechanism, the present application discloses a novel family of peptides of the general formula:

$$X_1-AA_4-X_2-AA_8-AA_9-AA_{10}-AA_{1\text{-}1}-AA_{12}-AA_{13}-X_3-AA_{20}-X_4$$ (I) wherein:

AA$_4$ is a bond or a neutral, nonpolar amino acid residue, preferably C, [D—C], A, [D—A] or desAA$_4$;

AA$_8$ is a bond or a basic polar amino acid residue, preferably R, [D—R], K, [D—K] or desAA$_8$;

AA$_9$ and AA$_{12}$ are each the same or different neutral nonpolar amino acid residues, preferably where AA$_9$ is I, [D—I], M, [D—M] or V and AA$_{12}$ is I, [D—I] or [D—V];

AA$_{10}$ is an acidic polar amino acid residue, preferably D, [D—D] or E;

AA$_{11}$ is a basic polar amino acid residue, preferably R or [D—R];

AA$_{13}$ is a bond or a neutral polar amino acid residue, preferably G, A, [D—A], Aib or desAA$_{13}$);

AA$_{20}$ is a bond or a neutral, polar or nonpolar amino acid residue, preferably C, [D—C], A, [D—A] or desAA$_{20}$;

X$_1$ is hydrogen, amido, acetyl, or additionally includes an amino acid, dipeptide, tripeptide or an oligopeptide of up to 125 amino acid residues, including Amino-terminal acetyl derivatives thereof;

X$_2$ is a valence bond, an amino acid or oligopeptide of up to 10, generally 5 and more usually 3 and preferably 2 or fewer amino acids;

X$_3$ is a valence bond, amino acid or oligopeptide of up to approximately 10 residues, more usually 6 and preferably 5 or fewer; and X4 is hydroxyl, amido, or additionally includes an amino acid, dipeptide, tripeptide or an oligopeptide of up to 20 amino acid residues, including Carboxy-terminal amide derivatives thereof;

and including compounds having an optional bond, preferably a disulfide bond, joining the residues AA4 and AA20, as indicated by the broken line, when these residues are each independently C or [D—C]; and wherein, for each amino acid residue or $X_n$ having amino acid residues or sequences of residues therein, each residue of the peptide can be any of the D-isomer or L-isomer; and each residue having the capability of being substituted with a substituent group, preferably an organic group including any of hydrogen or an aliphatic, aromatic or alkaryl group of from one to ten, usually one to six carbon atoms, including groups having substitutions of three or less nitrogen, oxygen or sulfur atoms as amido, thio or oxy, including hydroxy, thiol and ethers, wherein the ether is usually an alkyl ether, generally of one carbon atom, e.g. methyl;

with the proviso that either: when $X_2$ is a tripeptide, $X_3$ is not a hexapeptide, or when $X_2$ is a tripeptide and $X_3$ is a hexapeptide, at least one of AA4, AA8, AA13 or AA20 is desAA$_n$; which have natriuretic, diuretic, and/or hypotensive properties and thus, may have important therapeutic utility.

Although the foregoing invention has been described in some detail by way of clarity and for purposes of understanding, it will be understood by those skilled in the art that modifications of the invention may be practiced while remaining within the spirit and scope of the appended claims.

We claim:

1. A cyclic peptide useful as a natriuretic, diuretic, and/or vasodilator in mammals, of the formula:

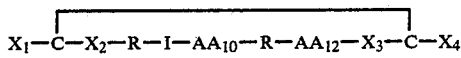

or

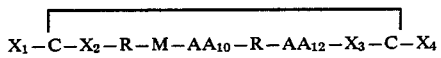

wherein the indicated bridge is a disulfide bridge between the two cysteine residues to which it is attached, and wherein AA10 is D or E,
AA12 is I or V,
$X_1$ is H, acetyl, or a peptide including the N-terminal acetylated forms thereof of 1-6 amino acids selected from the group consisting of S, L, R, and Y;
$X_2$ is a covalent bond or a peptide of 1-3 amino acids, wherein said amino acids are selected from the group consisting of F, G, A, S, and Aib;
$X_3$ is a covalent bond or is a peptide of 1-7 amino acid residues wherein said residues are selected from the group consisting of A, Q, S, G, L and Aib;
wherein $X_4$ is OH, NH2, or a peptide including the C-terminal amide derivatives thereof, of 1-5 amino acid residues wherein said amino acid residues are selected from the group consisting of N, S, F, R, and Y;
wherein one of the amino acid residues may optionally be in the D form;

with the proviso that when $X_2$ is a tripeptide, $X_3$ is not a heptapeptide, and when X is F—G, $X_3$ cannot be G—A—Q—S—G—L—G.

2. The peptide of claim 1 wherein the peptide of $X_1$ is selected from the group consisting of S—L—R—R—S—S, L—R—R—S—S, R—R—S—S, R—S—S, S—S, S, and R.

3. The peptide of claim 1 wherein the peptide of $X_2$ is selected from the group consisting of F—G—G, F—G—A, F—A—G, F—S—G, F—L—G, F—V—G, A—G—G, F—Aib—G, F—G, G—G, and G.

4. The peptide of claim 1 wherein the peptide of $X_3$ is selected from the group consisting of G—A—Q—S—G—L—G, A—Q—S—G—L—G, Q—S—G—L—G, S—G—L—G, G—L—G, L—G, G, G—A—Q—S—G—L, G—A—Q—S—G, G—A—Q—S, G—A—Q, G—A, A—Q—S—G—L, A—Q—S—G, A—Q—S, A—Q, A, Q—S—G—L, Q—S—G, Q—S, S, and Aib.

5. The peptide of claim 1 wherein the peptide of $X_4$ is selected from the group consisting of N—S—F—R—Y, N—S—F—R, N—S—F, N—S, and N, including the C-terminal amide derivatives thereof.

6. The peptide of claim 1 wherein AA10 is D and AA12 is I.

7. The peptide of claim 1 which is selected from the group consisting of:

| | |
|---|---|
| AP23 | R—S—S—C—G—G—R—I—D—R—I—G—A—Q—S—G—L—G—C—N—S—F—R—Y, |
| AP24 | R—S—S—C—G—R—I—D—R—I—G—A—Q—S—G—L—G—C—N—S—F—R—Y, |
| AP25 | R—S—S—C—R—I—D—R—I—G—A—Q—S—G—L—G—C—N—S—F—R—Y, |
| AP1 | R—S—S—C—F—G—G—R—I—D—R—I—G A—Q—S—G—C—N—S—F—R—Y, |
| AP3 | R—S—S—C—F—G—G—R—I—D—R—I—G—A—Q—S—C—N—S—F—R—Y, |
| AP4 | R—S—S—C—F—G—G—R—I—D—R—I—G—A—C—N—S—F—NH2, |
| AP17 | R—S—S—C—F—G—G—R—I—D—R—I—G—A—Q—C—N—S—F—R—Y, |
| AP20 | R—S—S—C—F—G—G—R—I—D—R—I—GA—C—N—S—F—R—Y, |
| AP21 | R—S—S—C—F—G—G—R—I—D—R—I—G—C—N—S—F—R—Y, |
| AP22 | R—S—S—C—F—G—G—R—I—D—R—I—C—N—S—F—R—Y, |
| AP36 | C—F—G—G—R—I—D—R—I—G—A—C, |
| AP37 | C—F—G—G—R—I—D—R—I—G—A—C—NH2, |
| AP62 | C—F—G—G—R—I—D—R—I—G—A—C—N—S—F—NH2, |
| AP109 | R—C—F—G—G—R—I—D—R—I—G—A—C—N—S—F—NH2, |
| AP110 | C—F—G—G—R—I—D—R—I—G—C—N—S—F—NH2, |
| AP64 | C—R—I—D—R—I—G—A—Q—S—G—L—G—C—NH2, |
| AP67 | C—F—G—G—R—I—D—R—I—G—A—Q—S—G—C—NH2, |
| AP69 | C—F—G—G—R—I—D—R—I—G—A—QC—NH2, |
| AP65 | C—R—I—D—R—I—G—A—Q—S—G—L—C—NH2, |
| AP70 | Y—C—F—G—G—R—I—D—R—I—G—A—C—NH2, |
| AP83 | C†—F—G—G—R—I—D—R—I—G—A—C—NH2, |
| AP57 | R—S—S—C—F—G—G—R—I—D—R—I—G—A—C—NH2 |
| AP91 | C—F†—G—G—R—I—D—R—I—G—A—C—NH2, |
| AP84 | C—F—A†—G—R—I—D—R—I—G—A—C—NH2, |
| AP85 | C—F—S†—G—R—I—D—R—I—G—A—C—NH2, |
| AP86 | C—F—L†—G—R—I—D—R—I—G—A—C—NH2, |
| AP111 | C—F—V†—G—R—I—D—R—I—G—A—C—NH2, |
| AP112 | C—F—Aib—G—R—I—D—R—I—G—A—C—NH2, |
| AP82 | C—F—G—G—R—I—D—R—I—G—Aib—C—NH2, |
| AP113 | C—F—G—G—R—M†—D—R—I—G—A—C—NH2, |
| AP94 | C—F—G—G—R—I—D—R—I—A†—A—C—NH2, |

| | |
|---|---|
| AP95 | C—F—G—G—R—I—D—R—I—G—A†—C—NH$_2$, |
| AP96 | C—F—G—G—R—I—D—R—I—G—A—C†—NH$_2$, |
| AP114 | C—A—G—G—R—I—D—R—I—G—A—C—NH$_2$, |
| AP115 | C—A†—G—G—R—I—D—R—I—G—A—C—NH$_2$, |
| AP88 | C—F—G—G—R†—I—D—R—I—G—A—C—NH$_2$, |
| AP89 | C—F—G—G—R—I†—D—R—I—G—A—C—NH$_2$, |
| AP90 | C—F—G—G—R—I—D†—R—I—G—A—C—NH$_2$, |
| AP92 | C—F—G—G—R—I—D—R†—I—G—A—C—NH$_2$, |
| AP93 | C—F—G—G—R—I—D—R—I†—G—A—C—NH$_2$, |
| AP116 | C—F—G—G—R—I—D—R—V†—G—A—C—NH$_2$, |
| AP117 | C—F—G—G—R—I—E—R—I—G—A—C—NH$_2$, |
| AP257 | C†—F—G—G—R—M—D—R—I—G—A—C—NH$_2$, |
| AP260 | C—F—L†—G—R—M—D—R—I—G—A—C—NH$_2$, |
| AP262 | C—F—G—G—R†—M—D—R—I—G—A—C—NH$_2$, |
| AP263 | C—F—G—G—R—M†—D—R—I—G—A—C—NH$_2$ |
| AP264 | C—F—G—G—R—M—D†—R—I—G—A—C—NH$_2$ |
| AP266 | C—F—G—G—R—M—D—R†—I—G—A—C—NH$_2$ |
| AP267 | C—F—G—G—R—M—D—R—I†—G—A—C—NH$_2$ |
| AP270 | C—F—G—G—R—M—D—R—I—G—A—C†—NH$_2$ |
| AP284 | C—F—V†—G—R—M—D—R—I—G—A—C—NH$_2$ |
| AP288 | C—F—G—G—R—M—D—R—V†—G—A—C—NH$_2$ |
| AP289 | C—F—G—G—R—M—E—R—I—G—A—C—NH$_2$ |
| AP76 | R—C—F—G—G—R—I—D—R—I—G—A—C—NH$_2$ | wherein the symbol for an amino acid superscripted by a dagger (†) indicates that the designated amino acid is in the D configuration.

8. A composition useful as a natriuretic, diuretic and/or vasodilator comprising a therapeutically effective amount of the compound of any of claims 1-6, together with a pharmaceutically acceptable carrier.

9. A method for inducing natriuresis, diuresis, or vasodilatation in a mammalian host, which comprises administering to said host a pharmaceutically effective amount of the composition of claim 8.

* * * * *